United States Patent
Pressly

(10) Patent No.: US 11,491,092 B2
(45) Date of Patent: Nov. 8, 2022

(54) HAIR TREATMENT FORMULATIONS AND USES THEREOF

(71) Applicant: Chembeau LLC, Santa Barbara, CA (US)

(72) Inventor: Eric D. Pressly, Santa Barbara, CA (US)

(73) Assignee: Chembeau LLC, Santa Barbara, CA (US)

(*) Notice: Subject to any disclaimer, the term of this patent is extended or adjusted under 35 U.S.C. 154(b) by 0 days.

(21) Appl. No.: 17/539,840

(22) Filed: Dec. 1, 2021

(65) Prior Publication Data

US 2022/0087913 A1    Mar. 24, 2022

Related U.S. Application Data

(63) Continuation of application No. PCT/US2021/042341, filed on Jul. 20, 2021.

(60) Provisional application No. 63/054,496, filed on Jul. 21, 2020.

(51) Int. Cl.

| | |
|---|---|
| *A61K 8/37* | (2006.01) |
| *A61K 8/22* | (2006.01) |
| *A61K 8/23* | (2006.01) |
| *A61Q 5/08* | (2006.01) |
| *A45D 7/06* | (2006.01) |
| *A61Q 5/06* | (2006.01) |

(Continued)

(52) U.S. Cl.
CPC .................. *A61K 8/37* (2013.01); *A45D 7/06* (2013.01); *A61K 8/22* (2013.01); *A61K 8/23* (2013.01); *A61Q 3/02* (2013.01); *A61Q 5/002* (2013.01); *A61Q 5/06* (2013.01); *A61Q 5/08* (2013.01); *A61K 2800/5922* (2013.01); *A61K 2800/882* (2013.01)

(58) Field of Classification Search
None
See application file for complete search history.

(56) References Cited

U.S. PATENT DOCUMENTS

| | | |
|---|---|---|
| 3,928,261 A | 12/1975 | Schertler |
| 4,150,115 A | 4/1979 | Jacquet et al. |
| 4,289,752 A | 9/1981 | Mahieu et al. |

(Continued)

FOREIGN PATENT DOCUMENTS

| | | | |
|---|---|---|---|
| CN | 104055699 A | | 9/2014 |
| DE | 1220969 | † | 7/1966 |

(Continued)

OTHER PUBLICATIONS

Alepee et al., 2013, Cosmetics Europe multi-laboratory pre-validation of the SkinEthic reconstituted human corneal epithelium test method for the prediction of eye irritation, Toxicology In Vitro, 27(5):1476-1488.

(Continued)

*Primary Examiner* — Nicole P Babson
(74) *Attorney, Agent, or Firm* — Knobbe, Martens, Olson & Bear, LLP

(57) ABSTRACT

The present application relates to hair treatment formulations and methods of use in the cosmetics field. The hair treatment formulations include bis(2-ethylhexyl) maleate as the active agent, and may be used in bleaching, conditioning and styling hair.

30 Claims, 6 Drawing Sheets

(51) Int. Cl.
*A61Q 3/02* (2006.01)
*A61Q 5/00* (2006.01)

(56) References Cited

U.S. PATENT DOCUMENTS

| | | |
|---|---|---|
| 4,445,521 A | 5/1984 | Grollier et al. |
| 4,719,099 A | 1/1988 | Grollier et al. |
| 5,206,012 A | 4/1993 | Farer et al. |
| 5,246,780 A | 9/1993 | Farer et al. |
| 5,266,322 A | 11/1993 | Myers et al. |
| 5,302,376 A | 4/1994 | Forestier et al. |
| 5,380,520 A | 1/1995 | Dobbs |
| 5,437,860 A | 8/1995 | Jarvis et al. |
| 5,468,477 A | 11/1995 | Kumar et al. |
| 5,489,431 A | 2/1996 | Ascione et al. |
| 5,518,728 A | 5/1996 | Burdzy |
| 5,599,524 A | 2/1997 | Morawsky et al. |
| 5,601,809 A | 2/1997 | Davis |
| 5,643,587 A | 7/1997 | Scancarella et al. |
| 5,665,364 A | 9/1997 | McAtee et al. |
| 5,688,831 A | 11/1997 | El Nokaly et al. |
| 5,698,649 A | 12/1997 | Meyer et al. |
| 5,731,450 A | 3/1998 | Alexander et al. |
| 5,747,018 A | 5/1998 | Valenty |
| 5,760,136 A | 6/1998 | Kato et al. |
| 5,853,712 A | 12/1998 | Langlois et al. |
| 5,871,754 A | 2/1999 | Briggs et al. |
| 5,939,054 A | 8/1999 | Msika et al. |
| 5,976,521 A | 11/1999 | Briggs et al. |
| 5,997,887 A | 12/1999 | Ha et al. |
| 6,001,373 A | 12/1999 | Igo Kemenes et al. |
| 6,013,269 A | 1/2000 | El Nokaly et al. |
| 6,013,270 A | 1/2000 | Hargraves et al. |
| 6,039,933 A | 3/2000 | Samain et al. |
| 6,063,397 A | 5/2000 | Fowler et al. |
| 6,090,403 A | 7/2000 | Block et al. |
| 6,123,933 A | 9/2000 | Hayama et al. |
| 6,139,849 A | 10/2000 | Lesaulnier et al. |
| 6,210,689 B1 | 4/2001 | Martino et al. |
| 6,238,650 B1 | 5/2001 | Lapidot et al. |
| 6,287,578 B1 | 9/2001 | Duetsch et al. |
| 6,306,373 B1 | 10/2001 | Impemate et al. |
| 6,355,261 B1 | 3/2002 | Bonda et al. |
| 6,361,768 B1 | 3/2002 | Galleguillos et al. |
| 6,368,606 B1 | 4/2002 | Dubief et al. |
| 6,375,932 B1 | 4/2002 | Hiwatashi et al. |
| 6,399,050 B1 | 6/2002 | Pasquet et al. |
| 6,410,005 B1 | 6/2002 | Galleguillos et al. |
| 6,432,908 B1 | 8/2002 | Dubief et al. |
| 6,436,375 B1 | 8/2002 | Lapidot et al. |
| 6,479,456 B1 | 11/2002 | Holzner |
| 6,485,732 B1 | 11/2002 | Bekele |
| 6,491,934 B1 | 12/2002 | Bekele |
| 6,495,150 B2 | 12/2002 | Bekele |
| 6,503,479 B1 | 1/2003 | LesAulnier et al. |
| 6,506,372 B1 | 1/2003 | Dubief et al. |
| 6,514,485 B1 | 2/2003 | Malpede et al. |
| 6,548,051 B2 | 4/2003 | Garnier et al. |
| 6,589,519 B1 | 7/2003 | Restle et al. |
| 6,589,542 B2 | 7/2003 | Bekele |
| 6,592,854 B1 | 7/2003 | Dupuis |
| 6,607,737 B2 | 8/2003 | Bekele et al. |
| 6,613,341 B2 | 9/2003 | Motley et al. |
| 6,626,962 B1 | 9/2003 | Lang et al. |
| 6,645,512 B2 | 11/2003 | Bekele |
| 6,673,336 B2 | 1/2004 | Buchholz et al. |
| 6,685,924 B2 | 2/2004 | Buchholz et al. |
| 6,716,419 B2 | 4/2004 | Zoltowski et al. |
| 6,762,158 B2 | 7/2004 | Lukenbach et al. |
| 6,864,330 B2 | 3/2005 | Schneider et al. |
| 6,872,401 B2 | 3/2005 | Seyler et al. |
| 6,992,120 B2 | 1/2006 | Silverman et al. |
| 7,150,764 B2 | 12/2006 | Plos et al. |
| 7,151,079 B2 | 12/2006 | Fack et al. |
| 7,179,880 B2 | 2/2007 | Kawa et al. |
| 7,211,268 B2 | 5/2007 | Dubief et al. |
| 7,223,385 B2 | 5/2007 | Gawtrey et al. |
| 7,297,678 B2 | 11/2007 | Kumar et al. |
| 7,387,795 B2 | 6/2008 | Hollenberg et al. |
| 7,572,435 B2 | 8/2009 | Kawa et al. |
| 7,585,513 B2 | 9/2009 | Belli |
| 7,713,310 B2 | 5/2010 | Lalleman |
| 7,758,888 B2 | 7/2010 | Lapidot et al. |
| 7,815,901 B2 | 10/2010 | Mathonneau et al. |
| 7,824,666 B2 | 11/2010 | Wolff et al. |
| 7,829,514 B2 | 11/2010 | Paul et al. |
| 7,879,113 B2 | 2/2011 | Simonet et al. |
| 7,909,888 B2 | 3/2011 | Hercouet et al. |
| 7,918,902 B2 | 4/2011 | Hercouet et al. |
| 7,927,381 B2 | 4/2011 | Hercouet |
| 7,927,383 B2 | 4/2011 | Hercouet et al. |
| 7,935,154 B2 | 5/2011 | Hercouet et al. |
| 7,947,089 B2 | 5/2011 | Hercouet et al. |
| 7,959,906 B2 | 6/2011 | Mougin |
| 7,976,831 B2 | 7/2011 | Fondin et al. |
| 8,066,781 B2 | 11/2011 | Hercouet et al. |
| 8,070,831 B2 | 12/2011 | Simonet et al. |
| 8,088,174 B2 | 1/2012 | Neplaz et al. |
| 8,148,561 B2 | 4/2012 | Ansmann et al. |
| 8,246,940 B2 | 8/2012 | Marie et al. |
| 8,287,846 B2 | 10/2012 | Rampoldi et al. |
| 8,309,065 B2 | 11/2012 | Ansmann et al. |
| 8,337,822 B2 | 12/2012 | Brun |
| 8,349,299 B2 | 1/2013 | Hu et al. |
| 8,354,096 B2 | 1/2013 | Banowski et al. |
| 8,399,001 B2 | 3/2013 | Laurent et al. |
| 8,419,807 B2 | 4/2013 | Ascione et al. |
| 8,545,817 B2 | 10/2013 | Beitone et al. |
| 8,545,821 B2 | 10/2013 | Maitra et al. |
| 8,580,285 B2 | 11/2013 | Falk et al. |
| 8,585,777 B2 | 11/2013 | Misu et al. |
| 8,671,956 B2 | 3/2014 | Bouchara et al. |
| 8,740,995 B1 | 6/2014 | Schweinsberg et al. |
| 8,747,824 B2 | 6/2014 | Nguyen-Kim et al. |
| 8,772,358 B2 | 7/2014 | Baseeth et al. |
| 8,778,032 B2 | 7/2014 | Schweinsberg et al. |
| 8,790,417 B2 | 7/2014 | Schweinsberg et al. |
| 8,790,623 B2 | 7/2014 | Lalleman et al. |
| 8,808,400 B2 | 8/2014 | Rapold et al. |
| 8,828,099 B2 | 9/2014 | Rapold et al. |
| 8,865,115 B2 | 10/2014 | Bechtloff et al. |
| 8,900,561 B2 | 12/2014 | Schulze zur Wiesche |
| 8,905,049 B2 | 12/2014 | Albert et al. |
| 8,936,779 B2 | 1/2015 | Pasquet et al. |
| 8,940,283 B2 | 1/2015 | Bebot |
| 8,940,943 B2 | 1/2015 | Beckedahl et al. |
| 8,961,620 B2 | 2/2015 | Rapold et al. |
| 9,005,594 B2 | 4/2015 | Hercouet et al. |
| 9,011,827 B2 | 4/2015 | Bui et al. |
| 9,044,411 B2 | 6/2015 | Knappe et al. |
| 9,060,944 B2 | 6/2015 | Charrier et al. |
| 9,095,520 B2 | 8/2015 | Banowski et al. |
| 9,109,068 B2 | 8/2015 | Rodrigues et al. |
| 9,119,973 B2 | 9/2015 | Warr et al. |
| 9,237,999 B2 | 1/2016 | Meder et al. |
| 9,248,088 B2 | 2/2016 | Harley et al. |
| 9,289,371 B2 | 3/2016 | Masuda et al. |
| 9,333,155 B1 | 5/2016 | Greco et al. |
| 9,456,978 B2 | 10/2016 | Suleiman et al. |
| 9,464,263 B2 | 10/2016 | Aussant et al. |
| 9,517,195 B2 | 12/2016 | Doring et al. |
| 9,539,192 B2 | 1/2017 | Odman Schmid et al. |
| 9,565,915 B2 | 2/2017 | DeGeorge et al. |
| 9,572,412 B2 | 2/2017 | Vic et al. |
| 9,585,820 B2 | 3/2017 | Lull et al. |
| 9,757,317 B2 | 9/2017 | Laughlin et al. |
| 9,861,572 B2 | 1/2018 | Doering |
| 9,889,417 B2 | 2/2018 | Baseeth |
| 9,980,885 B2 | 5/2018 | Watanabe et al. |
| 10,172,776 B2 | 1/2019 | Wang et al. |
| 10,266,656 B2 | 4/2019 | Wagner et al. |
| 10,322,078 B2 | 6/2019 | Yamada |
| 10,494,466 B2 | 12/2019 | Chuang et al. |
| 10,512,598 B2 | 12/2019 | Witte et al. |

(56) References Cited

U.S. PATENT DOCUMENTS

| | | |
|---|---|---|
| 10,561,599 B2 | 2/2020 | Patterson et al. |
| 10,611,933 B2 | 4/2020 | Song et al. |
| 10,653,611 B2 | 5/2020 | Alves et al. |
| 10,668,002 B2 | 6/2020 | Smith et al. |
| 10,682,303 B2 | 6/2020 | Fondin et al. |
| 2001/0055580 A1 | 12/2001 | Belli et al. |
| 2002/0059941 A1 | 5/2002 | Garnier et al. |
| 2002/0122781 A1 | 9/2002 | Pinzon et al. |
| 2002/0172655 A1 | 11/2002 | Hiwatashi et al. |
| 2002/0183217 A1 | 12/2002 | Perron et al. |
| 2002/0193265 A1 | 12/2002 | Perron et al. |
| 2002/0197225 A1 | 12/2002 | Giroud et al. |
| 2003/0026815 A1 | 2/2003 | Scott et al. |
| 2003/0053961 A1 | 3/2003 | Eccard |
| 2003/0113357 A1 | 6/2003 | Bell et al. |
| 2003/0147842 A1 | 8/2003 | Restle et al. |
| 2003/0161803 A1 | 8/2003 | Vic et al. |
| 2003/0175230 A1 | 9/2003 | Dubief |
| 2003/0206896 A1 | 11/2003 | O'Prey et al. |
| 2003/0206897 A1 | 11/2003 | O'Prey et al. |
| 2003/0211068 A1 | 11/2003 | O'Prey et al. |
| 2004/0042988 A1 | 3/2004 | Raney et al. |
| 2004/0042991 A1 | 3/2004 | Klug et al. |
| 2004/0109720 A1 | 6/2004 | Gruenbacher et al. |
| 2004/0146477 A1 | 7/2004 | Meffert et al. |
| 2004/0167046 A1 | 8/2004 | Lukenbach et al. |
| 2004/0208843 A1 | 10/2004 | Vic et al. |
| 2004/0228819 A1 | 11/2004 | Rabe et al. |
| 2004/0253283 A1 | 12/2004 | Muller et al. |
| 2005/0025737 A1 | 2/2005 | Sebagh et al. |
| 2005/0063933 A1 | 3/2005 | Vrignaud et al. |
| 2005/0118126 A1 | 6/2005 | Rollat et al. |
| 2005/0196362 A1 | 9/2005 | Carty et al. |
| 2006/0024255 A1 | 2/2006 | Quadir et al. |
| 2006/0062748 A1 | 3/2006 | Mathonneau |
| 2006/0088493 A1 | 4/2006 | Vic et al. |
| 2006/0177490 A1 | 8/2006 | Massouda |
| 2006/0228317 A1 | 10/2006 | Chrisstoffels et al. |
| 2006/0239946 A1 | 10/2006 | Samain et al. |
| 2006/0246119 A1 | 11/2006 | Eknoian et al. |
| 2007/0098770 A1 | 5/2007 | Shikinami et al. |
| 2007/0184001 A1 | 8/2007 | Vrignaud et al. |
| 2007/0231355 A1 | 10/2007 | Quadir et al. |
| 2008/0014166 A1 | 1/2008 | Klug et al. |
| 2008/0124282 A1 | 5/2008 | Emmerling et al. |
| 2008/0124295 A1 | 5/2008 | Duranton et al. |
| 2008/0206164 A1 | 8/2008 | Rollat-Corvol et al. |
| 2008/0206177 A1 | 8/2008 | Cothias |
| 2008/0286218 A1 | 11/2008 | Giroud et al. |
| 2009/0053290 A1 | 2/2009 | Sand et al. |
| 2009/0130028 A1 | 5/2009 | Rollat-Corvol et al. |
| 2009/0220444 A1 | 9/2009 | Teckenbrock et al. |
| 2009/0252771 A1 | 10/2009 | Coccia et al. |
| 2009/0258072 A1 | 10/2009 | Schlossman et al. |
| 2009/0297467 A1 | 12/2009 | Laurent et al. |
| 2010/0021549 A1 | 1/2010 | Meyrueix et al. |
| 2010/0047296 A1 | 2/2010 | Banowski et al. |
| 2010/0158848 A1 | 6/2010 | Bebot et al. |
| 2010/0186764 A1 | 7/2010 | Pasquet et al. |
| 2010/0202998 A1 | 8/2010 | Ramos-Stanbury et al. |
| 2010/0236569 A1 | 9/2010 | Gawtrey et al. |
| 2010/0297036 A1 | 11/2010 | Feuillete |
| 2010/0322877 A1 | 12/2010 | Zofchak et al. |
| 2012/0107261 A1 | 5/2012 | Banowski et al. |
| 2012/0128616 A1 | 5/2012 | Voisin et al. |
| 2012/0225106 A1 | 9/2012 | Ross et al. |
| 2012/0240954 A1 | 9/2012 | Emmerling et al. |
| 2012/0328550 A1 | 12/2012 | De Boni et al. |
| 2013/0149270 A1 | 6/2013 | Bouchara et al. |
| 2013/0164248 A1 | 6/2013 | Khenniche |
| 2013/0251656 A1 | 9/2013 | Khenniche et al. |
| 2013/0255709 A1 | 10/2013 | Khenniche et al. |
| 2013/0289080 A1 | 10/2013 | Masse et al. |
| 2013/0336905 A1 | 12/2013 | Fares et al. |
| 2014/0196741 A1 | 7/2014 | Cabourg et al. |
| 2014/0248227 A1 | 9/2014 | Doering et al. |
| 2014/0261512 A1 | 9/2014 | Nordstrom et al. |
| 2014/0369947 A1 | 12/2014 | Plos et al. |
| 2015/0044155 A1 | 2/2015 | Schulze zur Wiesche et al. |
| 2015/0080338 A1 | 3/2015 | Lorant et al. |
| 2015/0118175 A1 | 4/2015 | Feuillette et al. |
| 2015/0139925 A1 | 5/2015 | Kamikawa et al. |
| 2015/0265525 A1 | 9/2015 | Benn et al. |
| 2015/0297481 A1 | 10/2015 | Wahler et al. |
| 2015/0320650 A1 | 11/2015 | Wahler et al. |
| 2015/0328102 A1† | 11/2015 | Pressly |
| 2015/0342857 A1 | 12/2015 | DeGeorge et al. |
| 2016/0000689 A1 | 1/2016 | Pasquet et al. |
| 2016/0120771 A1 | 5/2016 | Simonet et al. |
| 2017/0172902 A1 | 6/2017 | Puls et al. |
| 2017/0172905 A1 | 6/2017 | Puls et al. |
| 2017/0172908 A1 | 6/2017 | Puls et al. |
| 2017/0259087 A1 | 9/2017 | Jaouani et al. |
| 2017/0348553 A1 | 12/2017 | Schelges et al. |
| 2018/0078474 A1 | 3/2018 | Biato et al. |
| 2018/0098615 A1 | 4/2018 | George et al. |
| 2018/0265805 A1 | 9/2018 | Gerke et al. |
| 2018/0311138 A1* | 11/2018 | Huynh ............... A61K 8/86 |
| 2018/0345709 A1 | 12/2018 | Loccuier et al. |
| 2018/0369089 A1 | 12/2018 | Cognet et al. |
| 2018/0369096 A1 | 12/2018 | Agach et al. |
| 2019/0142710 A1 | 5/2019 | Hedren et al. |
| 2019/0175462 A1 | 6/2019 | Hodes et al. |
| 2019/0175477 A1 | 6/2019 | Le Maire et al. |
| 2020/0016045 A1 | 1/2020 | Aubert et al. |
| 2020/0022902 A1 | 1/2020 | Brac de la Perriere et al. |
| 2020/0093731 A1 | 3/2020 | Brac de la Perriere et al. |
| 2020/0101006 A1 | 4/2020 | Brac de la Perriere |
| 2020/0129395 A1 | 4/2020 | Noll et al. |
| 2020/0129396 A1 | 4/2020 | Koopmann et al. |
| 2020/0170896 A1 | 6/2020 | Banowski et al. |
| 2020/0170901 A1 | 6/2020 | Banowski et al. |
| 2020/0206100 A1 | 7/2020 | Erkens et al. |
| 2020/0206111 A1* | 7/2020 | Lee ..................... A61K 8/342 |
| 2020/0289602 A1 | 9/2020 | Wu et al. |
| 2020/0299459 A1 | 9/2020 | Ehlis |
| 2020/0308371 A1 | 10/2020 | Briegel et al. |
| 2020/0315945 A1 | 10/2020 | Gouse et al. |
| 2020/0323765 A1 | 10/2020 | Crofoot et al. |
| 2020/0337981 A1 | 10/2020 | Dimitrova et al. |
| 2020/0345599 A1 | 11/2020 | Son et al. |
| 2020/0345602 A1 | 11/2020 | Tsushima et al. |
| 2020/0345684 A1 | 11/2020 | Vialpando et al. |
| 2020/0347096 A1 | 11/2020 | Endo et al. |
| 2020/0353099 A1 | 11/2020 | Anderson et al. |
| 2020/0360317 A1 | 11/2020 | Ernst |
| 2020/0375858 A1 | 12/2020 | Pang |
| 2020/0383910 A1 | 12/2020 | Kisak et al. |
| 2020/0390669 A1 | 12/2020 | Eppler et al. |
| 2020/0390933 A1 | 12/2020 | Williams et al. |
| 2020/0390944 A1 | 12/2020 | Williams et al. |
| 2020/0392499 A1 | 12/2020 | Carr et al. |
| 2020/0395103 A1 | 12/2020 | Ramakrishnan et al. |
| 2020/0397676 A1 | 12/2020 | Trujillo et al. |
| 2021/0000837 A1 | 1/2021 | Kutok et al. |
| 2021/0000842 A1 | 1/2021 | Eini et al. |
| 2021/0000974 A1 | 1/2021 | Angel et al. |
| 2021/0009505 A1 | 1/2021 | Angel et al. |
| 2021/0022970 A1 | 1/2021 | Michel et al. |
| 2021/0046212 A1 | 2/2021 | Williams et al. |
| 2021/0047484 A1 | 2/2021 | Williams et al. |
| 2021/0071217 A1 | 3/2021 | Paullin et al. |

FOREIGN PATENT DOCUMENTS

| | | |
|---|---|---|
| EP | 0 608 989 | 8/1994 |
| EP | 0 748 623 | 5/1997 |
| EP | 0 797 979 | 9/1998 |
| EP | 0 774 248 | 2/1999 |
| EP | 1 005 323 | 11/2001 |
| EP | 1 148 863 | 6/2002 |
| EP | 1 066 024 | 10/2002 |
| EP | 1 173 138 | 3/2003 |
| EP | 1 117 377 | 4/2004 |

(56) References Cited

FOREIGN PATENT DOCUMENTS

| | | |
|---|---|---|
| EP | 1 189 577 | 8/2004 |
| EP | 1 233 747 | 9/2004 |
| EP | 1 214 043 | 11/2005 |
| EP | 1 321 130 | 11/2005 |
| EP | 1 357 887 | 3/2006 |
| EP | 1 435 226 | 4/2006 |
| EP | 1 488 779 | 5/2006 |
| EP | 1 331 917 | 10/2006 |
| EP | 1 537 850 | 1/2007 |
| EP | 1 366 745 | 3/2007 |
| EP | 1 506 764 | 4/2007 |
| EP | 1 506 763 | 7/2007 |
| EP | 1 506 765 | 7/2007 |
| EP | 1 506 766 | 7/2007 |
| EP | 1 336 401 | 8/2007 |
| EP | 1 532 965 | 8/2007 |
| EP | 1 592 319 | 10/2007 |
| EP | 1 488 778 | 12/2007 |
| EP | 1 652 510 | 4/2008 |
| EP | 1 455 745 | 7/2008 |
| EP | 1 743 000 | 7/2008 |
| EP | 1 456 279 | 8/2008 |
| EP | 1 513 491 | 2/2009 |
| EP | 1 754 468 | 4/2009 |
| EP | 1 629 827 | 5/2009 |
| EP | 1 513 483 | 9/2009 |
| EP | 1 727 596 | 9/2009 |
| EP | 1 357 884 | 4/2010 |
| EP | 1 799 189 | 5/2010 |
| EP | 2 201 928 | 6/2010 |
| EP | 1 141 056 | 8/2010 |
| EP | 1 884 261 | 10/2010 |
| EP | 1 562 538 | 11/2010 |
| EP | 1 902 751 | 4/2011 |
| EP | 1 972 330 | 9/2012 |
| EP | 2 370 050 | 5/2013 |
| EP | 2 442 781 | 9/2015 |
| EP | 1 629 828 | 4/2016 |
| EP | 2 275 104 | 5/2016 |
| EP | 1 629 829 | 1/2017 |
| EP | 2 191 866 | 4/2017 |
| EP | 2 785 309 | 7/2017 |
| EP | 2 979 685 | 7/2017 |
| EP | 3 027 168 | 7/2017 |
| EP | 1 997 473 | 8/2017 |
| EP | 2 632 424 | 8/2017 |
| EP | 2 632 425 | 8/2017 |
| EP | 2 916 803 | 8/2017 |
| EP | 2 863 861 | 10/2017 |
| EP | 1 593 368 | 11/2017 |
| EP | 2 846 758 | 11/2017 |
| EP | 2 846 759 | 11/2017 |
| EP | 1 584 327 | 2/2018 |
| EP | 2 934 461 | 2/2018 |
| EP | 2 934 465 | 2/2018 |
| EP | 2 475 432 | 6/2018 |
| EP | 2 618 801 | 6/2018 |
| EP | 3 154 509 | 7/2018 |
| EP | 1 920 755 | 8/2018 |
| EP | 3 035 905 | 9/2018 |
| EP | 2 882 402 | 10/2018 |
| EP | 3 157 494 | 10/2018 |
| EP | 2 756 066 | 11/2018 |
| EP | 2 646 002 | 2/2019 |
| EP | 2 991 612 | 4/2019 |
| EP | 3 273 934 | 4/2019 |
| EP | 2 956 115 | 10/2019 |
| EP | 3 174 517 | 11/2019 |
| EP | 2 832 442 | 1/2020 |
| EP | 2 991 611 | 4/2020 |
| EP | 3 256 101 | 6/2020 |
| EP | 3 277 252 | 8/2020 |
| FR | 2842099 A1 | 1/2004 |
| WO | WO 95/004537 | 2/1995 |
| WO | WO 96/003962 | 2/1996 |
| WO | WO 98/020846 | 5/1998 |
| WO | WO 99/006014 | 2/1999 |
| WO | WO 00/015182 | 3/2000 |
| WO | WO 00/018359 | 4/2000 |
| WO | WO 01/000146 | 1/2001 |
| WO | WO 01/03973 | 1/2001 |
| WO | WO 02/022099 | 3/2002 |
| WO | WO 02/022102 | 3/2002 |
| WO | WO 03/104183 | 12/2003 |
| WO | WO 04/078149 | 9/2004 |
| WO | WO 06/056692 | 6/2006 |
| WO | WO 07/099269 | 9/2007 |
| WO | WO 07/099271 | 9/2007 |
| WO | WO 07/099272 | 9/2007 |
| WO | WO 08/155391 | 12/2008 |
| WO | WO 09/101000 | 8/2009 |
| WO | WO 10/049623 | 5/2010 |
| WO | WO 10/076483 | 7/2010 |
| WO | WO 10/076490 | 7/2010 |
| WO | WO 10/145921 | 12/2010 |
| WO | WO 11/002278 | 1/2011 |
| WO | WO 11/117403 | 9/2011 |
| WO | WO 11/128308 | 10/2011 |
| WO | WO 11/133511 | 10/2011 |
| WO | WO 11/157796 | 12/2011 |
| WO | WO 12/010684 | 1/2012 |
| WO | WO 12/035065 | 3/2012 |
| WO | WO 12/038534 | 3/2012 |
| WO | WO 12/038538 | 3/2012 |
| WO | WO 12/055805 | 5/2012 |
| WO | WO 12/055812 | 5/2012 |
| WO | WO 12/062755 | 5/2012 |
| WO | WO 12/084970 | 6/2012 |
| WO | WO 12/146527 | 11/2012 |
| WO | WO 13/060707 | 5/2013 |
| WO | WO 13/069165 | 5/2013 |
| WO | WO 13/069166 | 5/2013 |
| WO | WO 13/069167 | 5/2013 |
| WO | WO 13/069168 | 5/2013 |
| WO | WO 13/092719 | 6/2013 |
| WO | WO 13/092721 | 6/2013 |
| WO | WO 13/131856 | 9/2013 |
| WO | WO 13/153677 | 10/2013 |
| WO | WO 13/160440 | 10/2013 |
| WO | WO 14/023675 | 2/2014 |
| WO | WO 14/037306 | 3/2014 |
| WO | WO 14/091012 | 6/2014 |
| WO | WO 14/098254 | 6/2014 |
| WO | WO 14/187576 | 11/2014 |
| WO | WO 14/207097 | 12/2014 |
| WO | WO 15/028461 | 3/2015 |
| WO | WO 15/140472 | 9/2015 |
| WO | WO 16/035871 | 3/2016 |
| WO | WO 16/035872 | 3/2016 |
| WO | WO 17/081125 | 5/2017 |
| WO | WO 17/183562 | 10/2017 |
| WO | WO 18/115058 | 6/2018 |
| WO | WO 18/211069 | 11/2018 |
| WO | WO 18/234444 | 12/2018 |
| WO | WO 19/016153 | 1/2019 |
| WO | WO 19/016173 | 1/2019 |
| WO | WO 19/034573 | 2/2019 |
| WO | WO 19/096820 | 5/2019 |
| WO | WO 19/096821 | 5/2019 |
| WO | WO 19/115058 | 6/2019 |
| WO | WO 19/115706 | 6/2019 |
| WO | WO 19/129683 | 7/2019 |
| WO | WO 19/129703 | 7/2019 |
| WO | WO 19/155899 | 8/2019 |
| WO | WO 19/166140 | 9/2019 |
| WO | WO 19/178768 | 9/2019 |
| WO | WO 20/002434 | 1/2020 |
| WO | WO 20/002658 | 1/2020 |
| WO | WO 20/042138 | 3/2020 |
| WO | WO 20/127069 | 6/2020 |
| WO | WO 20/127346 | 6/2020 |
| WO | WO 20/127755 | 6/2020 |
| WO | WO 20/127759 | 6/2020 |
| WO | WO 20/127760 | 6/2020 |

(56) References Cited

FOREIGN PATENT DOCUMENTS

| | | |
|---|---|---|
| WO | WO 20/127766 | 6/2020 |
| WO | WO 20/127768 | 6/2020 |
| WO | WO 20/127835 | 6/2020 |
| WO | WO 20/127891 | 6/2020 |
| WO | WO 20/182951 | 9/2020 |
| WO | WO 20/201439 | 10/2020 |
| WO | WO 20/214854 | 10/2020 |
| WO | WO 20/214855 | 10/2020 |
| WO | WO 20/218022 | 10/2020 |
| WO | WO 20/219729 | 10/2020 |
| WO | WO 20/222029 | 11/2020 |
| WO | WO 20/227515 | 11/2020 |
| WO | WO 20/234675 | 11/2020 |
| WO | WO 20/242893 | 12/2020 |
| WO | WO 20/247594 | 12/2020 |
| WO | WO 20/247887 | 12/2020 |
| WO | WO 21/003462 | 1/2021 |
| WO | WO 21/005417 | 1/2021 |
| WO | WO 21/009040 | 1/2021 |
| WO | WO 21/022377 | 2/2021 |
| WO | WO 21/023885 | 2/2021 |
| WO | WO 21/035087 | 2/2021 |
| WO | WO 21/042044 | 3/2021 |

OTHER PUBLICATIONS

Asturiol et al., 2016, Consensus of classification trees for skin sensitization hazard prediction, Toxicology In Vitro, 36:197-209.

Bauch et al., 2012, Putting the parts together: Combining in vitro methods to test for skin sensitizing potentials, Regulatory Toxicology and Pharmacology, 63(3):489-504.

Chen et al., 2011, UHPLC determination of diethyl maleate in cosmetics, Lihua Jianyan, Huaxue Fence, 47(3):342-343.

Cho et al., 2014, Method for detecting the reactivity of chemicals towards peptides as an alternative test method for assessing skin sensitization potential, Toxicology Letters, 225(1):185-191 and errata.

Cho et al., 2019, High-throughput screening (HTS)-based spectrophotometric direct peptide reactivity assay (Spectro-DPRA) to predict human skin sensitization potential, Toxicology Letters, 314:27-36.

Cho et al., Aug. 2019, Application of Spectro-DPRA, KeratinoSens and h-CLAT to estimation of the skin sensitization potential of cosmetics ingredients, Journal of Applied Toxicology, 40(2):300-312.

Clouet et al., 2017, Comparison and validation of an in vitro skin sensitization strategy using a data set of 33 chemical references, Toxicology In Vitro, 45(Part 3):374-385.

Gregoire et al., 2017, Solvent Solubility Testing of Cosmetics-Relevant Chemicals: Methodology and Correlation of Water Solubility to In Silico Predictions, Journal of Solution Chemistry, 46(7):1349-1363.

Kouzuki et al., 2009, Development of an in silico prediction system for the risk assessment of chemicals: development of prediction models for skin sensitization and repeated dose toxicity, Nippon Koshohin Gakkaishi, 33(2):65-73.

Li et al., Nov. 2013, Determination of diethyl maleate in cosmetics by rapid resolution liquid chromatography-tandem mass spectrometry, Journal of Chinese Mass Spectrometry Society, 34(6):362-366.

Mbah, 2007, Studies on the lipophilicity of vehicles (or co-vehicles) and botanical oils used in cosmetic products, Pharmazie, 62(5):351-353.

McKim et al., 2010, A new in vitro method for identifying chemical sensitizers combining peptide binding with ARE/EpRE-mediated gene expression in human skin cells, Cutaneous and Ocular Toxicology, 29(3):171-192.

Mundschau et al., Jul. 3, 2013, Formulating for delivery from elastomeric nonwoven substrates, Cosmetics & Toiletries, 126(4):284-289.

Natsch et al., 2008, Skin sensitizers induce antioxidant response element dependent genes: application to the in vitro testing of the sensitization potential of chemicals, Toxicological Sciences, 102(1):110-119.

Natsch et al., Apr. 2013, A dataset on 145 chemicals tested in alternative assays for skin sensitization undergoing prevalidation, Journal of Applied Toxicology, 33(11):1337-1352.

Natsch et al., 2009, Filling the Concept with Data: Integrating Data from Different In Vitro and In Silico Assays on Skin Sensitizers to Explore the Battery Approach for Animal-Free Skin Sensitization Testing, Toxicological Sciencex, 107(1):106-121.

Opdyke, 1976, Monographs on fragrance raw materials. Diethyl maleate, Food and Cosmetics Toxicology, 14(5):443-444.

Research Disclosure, Oct. 2006, High spreading ester emollient for body care concepts, p. 1284-1286.

Research Disclosure, Oct. 2006, High spreading ester emollient for water-in oil concepts,. p. 1307.

Roberts et al., 2007, Mechanistic Applicability Domain Classification of a Local Lymph Node Assay Dataset for Skin Sensitization, Chemical Research in Toxicology, 20(7):1019-1030.

Tourneix et al., 2019, Assessment of a defined approach based on a stacking prediction model to identify skin sensitization hazard, Toxicology in Vitro, 60:134-143.

Tourneix et al., 2020, Skin sensitisation testing in practice: Applying a stacking meta model to cosmetic ingredients, Toxicology In Vitro, 66:104831.

PCT International Search Report and Written Opinion for PCT/US2021/042341, dated Sep. 8, 2021.

Albano-Garcia et al. (1980) Coconut fatty amines and their quaternary ammonium salts. Phil. J. Coco. Stud. V:2:13-19. https://agris.fao.org/agris-seareh/search.do?recordID=XB8110082.

Cocamidopropyl Dimethylamine. INCI Decoder (Copyright 2022) https://incidecoder.com/ingredients/cocamidopropyl-dimethylamine.

\* cited by examiner
† cited by third party

HAIR TREATMENT FORMULATIONS AND USES THEREOF

INCORPORATION BY REFERENCE TO PRIORITY APPLICATION

The present application is a continuation of International application No. PCT/US2021/042341, filed Jul. 20, 2021, which claims the benefit of priority to U.S. provisional application No. 63/054,496, filed Jul. 21, 2020, each of which is incorporated by reference in its entirety.

BACKGROUND

Field

The present application generally relates to cosmetic and personal care formulations, kits and methods of use thereof. Particularly the application is related to cosmetic formulations for hair treatment.

Description of the Related Art

Hair is a protein filament that grows from follicles found in the dermis. Hair is primarily composed of proteins, notably alpha-keratin. Alpha-keratin is a fibrous structural protein (polypeptide chain), which is made up of amino acids that form a repeating secondary structure such as alpha-helix. These alpha-helix chains of amino acids are typically bound to each other by hydrogen bonds, salt bridges, and/or disulfide bonds. Color treatments include hair coloring, highlighting, and bleaching. The coloring products can be categorized in several types, which include permanent, demi-permanent, semi-permanent, and temporary coloring formulations.

Various approaches to hair dyeing have been developed including oxidative dyes, direct action dyes, natural dyes, metallic dyes and reactive dyes. Many hair coloring formulations, such as oxidative dyes, are utilized at an elevated pH in order to open the hair cuticle and allow deeper penetration of the dye precursors. Additionally, standard bleach formulations use a mixture of high pH persulfates and hydrogen peroxide to oxidize melanin within hair. However, these processes can leave the hair frizzy and damaged.

Furthermore, at alkaline pH (for example when lye-based relaxers are used on hair) protein secondary structures within the hair are broken so that straightening of the hair may be achieved. While alkali-based relaxers are effective at relaxing and straightening hair, they may result in a reduction of hair strength and a loss of hair through breakage. Alkaline conditions also damage the hair and may cause the cuticle of the hair strands to become roughened resulting in ruffled, tangled, and generally unmanageable hair that makes hair look lusterless and dull.

Yet another issue with the use of alkali-based hair relaxers is that their application leads to completely relaxed and straightened hair without any method to retain the level of curl. Furthermore, due to the reduction of hair strength and potential loss of hair due to breakage from such relaxing processes, any further application of a permanent wave process (i.e., to introduce a controlled amount of curl) to the already relaxed and straightened hair would result in further damage and/or breakage of the hair.

In addition, traditional perms use thiol or sulfur-containing reducing agents followed by a second oxidizing step, typically using hydrogen peroxide, to set the hair. However, these thiol or sulfur-containing reducing agents are foul smelling and, if not properly rinsed between the steps, can damage and/or break hair.

Previous work described in U.S. Pat. No. 9,326,926 utilizes an acidic keratin treatment to reduce hair damages caused by hair treatment, and previous work described in U.S. Pat. No. 9,713,583 utilizes an acidic keratin treatment with maleic acid or a maleate salt (e.g. bis-aminopropyl diglycol dimaleate) to effect the curl of hair. However, the active agents in the keratin treatment are very acidic and may be incompatible with the hair treatment formulations such as hair bleach and oxidative hair coloring formulations, which require a high pH to be effective. As such, careful and proper mixing of the acidic keratin treatment is required to not substantially alter the pH and the performance of the bleaching and coloring formulations. As such, there remains a need to develop a convenient to use yet effective hair treatment can reduce hair damages during hair treatment and improve hair condition.

SUMMARY

Some aspect of the present disclosure relates to a cosmetic or personal care formulation. The cosmetic formulation includes: a compound of Formula (I) or Formula (II), or a combination thereof, having the structure:

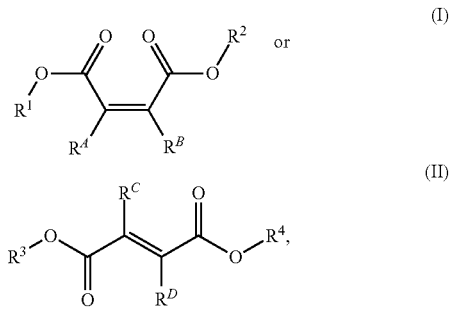

wherein: each of $R^1$, $R^2$, $R^3$ and $R^4$ is independently selected from the group consisting of an optionally substituted $C_1$-$C_{22}$ alkyl, an optionally substituted $C_2$-$C_{22}$ alkenyl, an optionally substituted $C_2$-$C_{22}$ alkynyl, an optionally substituted $C_3$-$C_{10}$ carbocyclyl, an optionally substituted $C_6$-$C_{10}$ aryl, an optionally substituted 5 to 10 membered heteroaryl, an optionally substituted 3 to 10 membered heterocyclyl, and an optionally substituted $C_2$-$C_{22}$ alkoxyalkyl; and each of $R^A$, $R^B$, $R^C$ and $R^D$ is independently hydrogen or an optionally substituted $C_1$-$C_{22}$ alkyl; and a cosmetically acceptable carrier or excipient, or a combination thereof.

In some embodiments of the cosmetic or personal care formulation described herein, each of $R^1$, $R^2$, $R^3$ and $R^4$ is independently selected from the group consisting of an optionally substituted $C_1$-$C_{22}$ alkyl, an optionally substituted $C_2$-$C_{22}$ alkenyl, and an optionally substituted $C_2$-$C_{22}$ alkynyl. In some embodiments, each of $R^1$, $R^2$, $R^3$ and $R^4$ is independently an optionally substituted $C_1$-$C_{22}$ alkyl. In some embodiments, each of $R^A$, $R^B$, $R^C$ and $R^D$ is hydrogen. In some further embodiments, each of $R^1$ and $R^2$ is independently an unsubstituted $C_1$-$C_6$ alkyl (e.g., methyl, ethyl, propyl, isopropyl, n-butyl, isobutyl, t-butyl, n-pentyl, isopentyl, n-hexyl, or isohexyl), and each of $R^A$ and $R^B$ is hydrogen. In one embodiment, each of $R^1$ and $R^2$ is n-butyl. In some further embodiments, each of $R^3$ and $R^4$ is independently an unsubstituted $C_1$-$C_6$ alkyl (e.g., methyl, ethyl, propyl, isopropyl, n-butyl, isobutyl, t-butyl, n-pentyl, isopentyl, n-hexyl, or isohexyl), and each of $R^C$ and $R^D$ is hydrogen. In one embodiment, each of $R^3$ and $R^4$ is n-butyl. In some further embodiments, each of $R^1$ and $R^2$ is independently an unsubstituted $C_7$-$C_{12}$ alkyl (e.g., n-heptyl, iso-heptyl, n-octyl, iso-octyl, ethylhexyl, n-nonyl, isononyl, n-decyl, iso-decyl, ethyloctyl), and each of $R^A$ and $R^B$ is hydrogen. In one embodiment, each of $R^1$ and $R^2$ is octyl or ethylhexyl. In some further embodiments, each of $R^3$ and $R^4$ is independently an unsubstituted $C_7$-$C_{12}$ alkyl (e.g., n-heptyl, iso-heptyl, n-octyl, iso-octyl, ethylhexyl, n-nonyl, isononyl, n-decyl, iso-decyl, ethyloctyl), and each of $R^C$ and $R^D$ is hydrogen. In one embodiment, each of $R^3$ and $R^4$ is octyl or ethylhexyl.

In some embodiments of the cosmetic or personal care formulation described herein, the cosmetic formulation comprises the compound of Formula (I). In some embodiments, the cosmetic formulation comprises the compound of Formula (II). In some embodiments, the cosmetic formulation comprises about 0.1 wt. % to about 50 wt. % or 0.5 wt. % to about 25 wt. % of the compound of (I) or (II) or a combination thereof. In some embodiments, the cosmetic formulation comprises at least about 0.5 wt. %, 1 wt. %, 2 wt. %, 3 wt. %, 4 wt. %, 5 wt. %, 6 wt. %, 7 wt. %, 8 wt. %, 9 wt. %, or 10 wt. % of compound of (I) or (II) or a combination thereof. In some further embodiments, the cosmetic or personal care formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof. In some embodiments, the cosmetic formulation further comprises one or more pH modifying agents. In some embodiments, the cosmetically acceptable carrier comprises water, ethyl acetate, acetone, alcohol, polyol, oil, silicone, liposomes, or ester, or combinations thereof. In some embodiments, the polyol comprises or is glycol.

In some embodiments of the cosmetic or personal care formulation described herein, the cosmetically acceptable excipient may comprises a surfactant, a vitamin, a natural extract, a preservative, an antioxidant, a chelating agent, a protein, an amino acid, a humectant, a fragrance, an emollient, a penetrant, a thickener, a viscosity modifier, a hair fixative, a film former, an emulsifier, an opacifying agent, a propellant, a carrier, a salt, a buffer, an anti-static agent, an anti-frizz agent, an anti-dandruff agent, or a colorant, or combinations thereof. In some embodiments, the cosmetic formulation is in the form of a gel, liquid, cream, powder, emulsion, liposome, or lotion.

In some embodiments of the cosmetic or personal care formulation described herein, the cosmetic formulation comprises or is a hair treatment formulation, a skin treatment formulation, a nail treatment formulation, or combinations thereof. In further embodiments, the cosmetic formulation is a hair treatment formulation, for example, a hair bleaching formulation, a hair damage repair formulation, a hair styling formulation, or a hair straightening formulation, etc. A particular embodiment of the cosmetic formulation described herein is a hair bleaching formulation comprising: about 1% wt. to about 12% wt. of hydrogen peroxide; about 10% wt. to about 40% wt. of one or more persulfate salts; and about 0.5 wt. % to about 20 wt. %, or about 1% wt. to about 10% wt. of a compound of Formula (I) or (II) or a combination thereof. In some further embodiments, the cosmetic formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof.

In any embodiments of the cosmetic or personal care formulation described herein, the formulation may be in a cosmetic or personal care kit. In some embodiments of the kit described herein, the kit is a hair care kit and the kit may further comprise one or more hair treatment agents. In some embodiments, the one or more hair treatment agents are separated from the cosmetic formulation described herein. In some embodiments, the one or more hair treatment agents comprises a bleaching agent, a relaxing agent, a coloring agent, a shampooing agent, or a conditioning agent, or combinations thereof. In some embodiments, the bleaching agent comprises one or more persulfate salts, or one or more peroxides (such as hydrogen peroxide), or a combination thereof. In some embodiments, the persulfate salt comprises or is potassium persulfate, ammonium persulfate, or sodium persulfate, or combinations thereof. In some embodiments, the one or more persulfates has a basic pH of at least about 8, 9 or 10. In some embodiments, the hydrogen peroxide is in a solution having an acid pH of about 3, 4 or 5 (e.g., 3.5). In some embodiments, the relaxing agent comprises sodium hydroxide, lithium hydroxide, potassium hydroxide, guanidinium hydroxide, ammonium hydroxide, a sulfite salt, or a thioglycolate salt, or combinations thereof. In some embodiments, the sulfite salt is sodium sulfite or potassium sulfite or a combination thereof.

In some other embodiments of the kit described herein, the kit is a nail care kit and the kit may further comprise one or more nail treatments or coloring agents. In some such embodiment, the cosmetic formulation comprises the compound of Formula (I) or (II) or a combination thereof is a nail polish. In other embodiments, the cosmetic formulation is in the form of a colorless nail base or primer, which is applied as a base coat prior to the application of one or more nail polish containing coloring agents.

Some other aspect of the present disclosure relates to a method of bleaching hair, comprising applying a cosmetic formulation to the hair, wherein the cosmetic formulation comprises a bleaching formulation, and a compound of Formula (I) or (II), or a combination thereof as described herein. In some embodiments, the amount of compound of Formula (I) or (II) in the cosmetic formulation is at least about 0.5% by weight; and wherein in the cosmetic formulation has a basic pH of greater than about 9. In some embodiments, the cosmetic formulation comprises at least about 1% by weight of the compound of Formula (I) or (II). In some embodiments, the method further comprises combining the bleaching formulation and the compound of Formula (I) or (II) to form the cosmetic formulation. In some embodiments, the cosmetic formulation is formed within about 1 to 3 hours before being applied to the hair. In other embodiments, the cosmetic formulation is formed within about 30 minutes or less before being applied to the hair. In some embodiments, the cosmetic formulation is formed on hair by applying the formulation and the compound of Formula (I) or (II) on the hair, either sequentially or simultaneously. As such, the step of applying the cosmetic formulation to the hair comprises applying the bleaching formulation and the compound of Formula (I) or (II) on the hair to form the cosmetic formulation. In some embodiments, the compound of Formula (I) or (II) is in a separate composition comprising at least 5% to 10% of one or more surfactants (for example, a cationic surfactant such as behentrimonium chloride and/or behentrimonium methosulfate) prior to combining with the bleaching formulation. As such, the cosmetic formulation is formed by combining the beaching formulation with the composition comprising the compound of Formula (I) or (II). In some embodiments, the method further comprises rinsing the hair after applying the cosmetic formulation. In further embodiments, the cosmetic formulation comprises about 0.2 wt. % to about 60 wt. %, about 0.5 wt. % to about 40 wt. %, about 1 wt. % to about 30 wt. %, about 2 wt. % to about 20 wt. %, or about 3 wt. % to about 15 wt. %, or about 5 wt. % to about 10 wt. % of the compound of Formula (I) of (II). In further embodiments, the bleaching formulation comprises one or more persulfate salts, or hydrogen peroxide, or a combination thereof. In some such embodiments, the persulfate salt comprises or is potassium persulfate, ammonium persulfate, or sodium persulfate, or combinations thereof. In some embodiments, the cosmetic formulation further comprises one or more cosmetically acceptable excipients selected from the group consisting of a surfactant, a vitamin, a natural extract, a preservative, an antioxidant, a chelating agent, a protein, an amino acid, a humectant, a fragrance, an emollient, a penetrant, a thickener, a viscosity modifier, a hair fixative, a film former, an emulsifier, an opacifying agent, a propellant, a carrier, a salt, a buffer, an anti-static agent, an anti-frizz agent, an anti-dandruff agent, and a colorant, and combinations thereof. In some embodiments, the cosmetic formulation is in the form of a gel, liquid, cream, powder, or lotion. In some further embodiments, the breakage of the hair is decreased by at least 5%, 10%, 15% or 20%, compared to hair bleached with the bleaching formulation in the absence of the compound of Formula (I) or (II). In some further embodiments, the cosmetic formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof.

Some other aspect of the present disclosure relate to a method of treating hair to reduce or prevent hair breakage, comprising: applying a hair treatment formulation to damaged hair, wherein the hair treatment formulation comprises a compound of Formula (I) or (II) or a combination thereof, and a cosmetically acceptable carrier. In some embodiments, the amount of compound of Formula (I) or (II) in the hair treatment formulation is at least about 0.1%, 0.2%, 0.3%, 0.4%, 0.5%, 1%, 2%, 3%, 4%, 5%, 6%, 7%, 8%, 9%, 10%, 15%, 20%, 25%, 30%, 35%, 40%, 45%, 50%, 55%, 60% or 70% by weight, or a range defined by any two of the preceding values. In further embodiments, the amount of compound of Formula (I) or (II) in the hair styling formulation is at least about 0.5% or 1% by weight. In further embodiments, breakage of the hair is decreased by at least 5% compared to untreated hair. In some embodiments, the damaged hair is caused by bleaching, relaxing, coloring, perming, straightening, or heat styling, or combination thereof. In further embodiments, the amount of compound of Formula (I) or (II) in the hair treatment formulation is at least about 1%, 2%, 3%, 4%, 5%, 6%, 7%, 8%, 9% or 10% by weight. For example, the amount of compound of Formula (I) or (II) in the hair treatment formulation is at least about 5% to about 10% when the hair is coarse or heavily damaged (e.g., have been previously subject to repeated coloring, bleaching, perming, relaxing, straightening, or heat styling, etc.). In some embodiments, the hair treatment formulation is formed by mixing the compound of Formula (I) or (II) in a cosmetically acceptable carrier. In some such embodiments, the cosmetically acceptable carrier comprises or is water, purified water, or deionized water. In some embodiments, the compound of Formula (I) or (II) is in a separate composition comprising at least 5% to 10% of one or more surfactants (for example, a cationic surfactant such as behentrimonium chloride and/or behentrimonium methosulfate) prior to mixing with the cosmetically acceptable carrier. As such, the hair treatment formulation is formed by combining the composition comprising the compound of Formula (I) or (II) with the cosmetically acceptable carrier (e.g., purified water). In some embodiments, the method further comprises rinsing the hair after applying the hair treatment formulation. In other embodiments, the method does not require rinsing the hair after applying the hair treatment formulation. In further embodiments, applying the hair treatment formulation comprises spraying the hair treatment formulation onto the damage hair. In some embodiments, the hair treatment formulation is applied to the hair 1, 2, 3, 4, 5, 6, 7, 8, 9 or 10 times a week, to achieve the decreased hair breakage and improved hair quality over time. For example, hair breakage may be decreased by at least 10%, 15%, 20%, 25%, 30%, 35%, 40%, 45%, 50% compared to untreated hair, when the hair treatment formulation is used at least 2-3 times/week for at least 1, 2, 3, 4, 5 or 6 months. In some embodiments, the hair treatment formulation further comprises one or more cosmetically acceptable excipients selected from the group consisting of a surfactant, a vitamin, a natural extract, a preservative, an antioxidant, a chelating agent, a protein, an amino acid, a humectant, a fragrance, an emollient, a penetrant, a thickener, a viscosity modifier, a hair fixative, a film former, an emulsifier, an opacifying agent, a propellant, a carrier, a salt, a buffer, an anti-static agent, an anti-frizz agent, an anti-dandruff agent, and a colorant, and combinations thereof. In some further embodiments, the hair treatment formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof.

Some additional aspect of the present disclosure relates to a method of styling hair, comprising: applying a hair styling formulation to the hair, wherein the hair styling formulation comprises a compound of Formula (I) or (II) or a combination thereof as described herein; and treating hair with a heated hair styling tool. In some embodiments, the method further comprises blow drying the hair prior to treating the hair with the heated styling tool. In further embodiments, the amount of compound of Formula (I) or (II) in the hair styling formulation is at least about 0.1%, 0.2%, 0.3%, 0.4%, 0.5%, 1%, 2%, 3%, 4%, 5%, 6%, 7%, 8%, 9%, 10%, 15%, 20%, 25%, 30%, 35%, 40%, 45%, 50%, 55%, 60% or 70% by weight, or a range defined by any two of the preceding values. In further embodiments, the amount of compound of Formula (I) or (II) in the hair styling formulation is at least about 0.5%, 1%, 2%, 3%, 4%, 5%, 6%, 7%, 8%, 9% or 10% by weight. For example, the amount of compound of Formula (I) or (II) in the hair styling formulation is at least about 5% to about 10% when the hair is coarse or heavily damaged (e.g., have been previously subject to repeated coloring, bleaching, perming, relaxing, straightening, or heat styling, etc.). In some embodiments, the method further comprises rinsing the hair after applying the hair styling formulation. In other embodiments, the method does not require rinsing the hair after applying the hair styling formulation. In some embodiments, the hair styling formulation is applied to the hair 1, 2, 3, 4, 5, 6, 7, 8, 9 or 10 times a week, to achieve the decreased hair breakage and improved hair quality over time. For example, hair breakage may be decreased by at least 10%, 15%, 20%, 25%, 30%, 35%, 40%, 45%, 50% compared to untreated hair, when the hair styling formulation is used at least 2-3 times/week for at least 1, 2, 3, 4, 5 or 6 months. In some embodiments, the hair styling formulation further comprises one or more cosmetically acceptable excipients selected from the group consisting of a surfactant, a vitamin, a natural extract, a preservative, an antioxidant, a chelating agent, a protein, an amino acid, a humectant, a fragrance, an emollient, a penetrant, a thickener, a viscosity modifier, a hair fixative, a film former, an emulsifier, an opacifying agent, a propellant, a carrier, a salt, a buffer, an anti-static agent, an anti-frizz agent, an anti-dandruff agent, and a colorant, and combinations thereof. In some further embodiments, the hair styling formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof.

Some additional embodiments relate to a method of perming hair, comprising: applying a reducing agent to the hair; washing, rinsing or shampooing the hair; and applying a perming formulation to the hair, wherein the perming formulation comprises a compound of Formula (I) or (II) or a combination thereof as described herein. In further embodiments, the amount of compound of Formula (I) or (II) in the perming formulation is at least about 0.5%, 1%, 2%, 3%, 4%, 5%, 6%, 7%, 8%, 9%, 10%, 15% or 20% by weight. For example, the amount of compound of Formula (I) or (II) in the perming formulation is at least about 5% to about 10% when the hair is coarse or heavily damaged (e.g., have been previously subject to repeated coloring, bleaching, perming, relaxing, straightening, or heat styling, etc.). In some embodiments, the method further comprises rinsing the hair after applying the perming formulation. In further embodiments, the method may also comprise styling hair with a heated hair styling tool. In some embodiments, the reducing agent comprises or is thioglycolic acid, thiolactic acid, dihydrolipoate, thioglycerol, mercaptopropionic acid, sodium bisulfite, ammonium bisulfide, zinc formaldehyde sulfoxylate, sodium formaldehyde sulfoxylate, sodium metabisulfite, potassium borohydride, pegylated thiols, or hydroquinone, or combinations thereof. In some embodiments, the reducing agent is applied to the hair prior to the perming formulation being applied to the hair. In some such embodiments, the perming formulation is applied to the hair at, at about, at most, at most about, at least, or at least about, 30 seconds, 1 minute, 5 minutes, 10 minutes, 15 minutes, 30 minutes, or 1 hour after the application of the reducing agent. In some other embodiments, the reducing agent is applied to the hair concurrently with the styling formulation. In some embodiments, the method further comprises washing, rinsing, or drying, or a combination thereof, of the hair after the application of the reducing agent and before the application of the perming formulation. In further embodiments, the perming formulation further comprises an oxidant (e.g., a peroxide). In some embodiments, the method may achieve decreased hair breakage and improved hair quality compared to a perming method when the perming formulation without the active agent (e.g., the compound of Formula (I) or (II)). For example, hair breakage may be decreased by at least 10%, 15%, 20%, 25%, 30%, 35%, 40%, 45%, 50% compared to using a perming formulation without the active agent. In some embodiments, the perming formulation further comprises one or more cosmetically acceptable excipients selected from the group consisting of a surfactant, a vitamin, a natural extract, a preservative, an antioxidant, a chelating agent, a protein, an amino acid, a humectant, a fragrance, an emollient, a penetrant, a thickener, a viscosity modifier, a hair fixative, a film former, an emulsifier, an opacifying agent, a propellant, a carrier, a salt, a buffer, an anti-static agent, an anti-frizz agent, an anti-dandruff agent, and a colorant, and combinations thereof. In some further embodiments, the perming formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof.

Some other aspect of the present disclosure relates to a method of treating nail, comprising: applying a nail treatment formulation to one or more nails, wherein the nail treatment formulation comprises a compound of Formula (I) or (II) or a combination thereof as described herein, and one or more volatile solvents. In some embodiments, the amount of the compound of Formula (I) or (II) in the nail treatment formulation is at least 0.1%, 0.2%, 0.3%, 0.4%, 0.5%, 1%, 2%, 3%, 4%, 5%, 6%, 7%, 8%, 9%, 10%, 15%, 20%, 25%, 30%, 35%, 40%, 45%, 50%, 55%, 60% or 70% by weight, or in a range defined by any two of the preceding values. In further embodiments, the amount of the compound of Formula (I) or (II) in the nail treatment formulation is at least about 5%, 6%, 7%, 8%, 9%, 10%, 15%, or 20% by weight. In some embodiments, the one or more volatile solvents comprise or is ethyl acetate, or acetone, or a combination thereof. In some embodiments, the method further comprises washing, rinsing, or drying, or a combination thereof, of one or more nails prior to the application of the nail treatment formulation. In some embodiments, the nail treatment formulation is applied to one or more nails as a nail base coat or a nail primer before applying a nail coloring agent. For example, the nail treatment formulation is applied to one or more nails for at least about 1 minute, 5 minutes, 10 minutes, or 1 hour prior to the application of the nail coloring agent. In some further embodiments, the nail treatment formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof.

DETAILED DESCRIPTION

Figure 1:
FIG. 1 is a photograph of hair swatches treated with cosmetic Formulae A, B or C (from left to right respectively).

The present application relates to cosmetic formulations, kits and methods of use thereof. The cosmetic formulation includes an effective amount of one or more diester compounds of Formula (I) or (II) as described herein, and a cosmetically acceptable carrier or excipient, or a combination thereof. The cosmetic formulation can be used to treat hair, skin and/or nails. For example, the cosmetic formulation can be used to treat hair or prevent damage to hair that is caused by hair treatments such as dyeing, bleaching, relaxing, straightening and/or perming hair.

In contrast to previously reported keratin treatments that contain acidic active agents, the diester compounds described herein are relatively pH neutral. As such, cosmetic formulations containing the diester compound(s) described herein may be liberally applied without affecting the effectiveness of high pH cosmetic co-treatments, such as hair bleaching and oxidative hair coloring, which require careful balance of pH for adequate performance and effectiveness. One main advantage of the cosmetic formulations described herein is that the amount of the pH neutral diester compounds used in the cosmetic treatment can be in a wide range without concern to the relative amount of other pH sensitive treatments, such as hair bleaching, hair coloring, hair relaxing, hair curling, or skin and nail treatments.

Definitions

Unless defined otherwise, all technical and scientific terms used herein have the same meaning as is commonly understood by one of ordinary skill in the art.

The use of the term "including" as well as other forms, such as "include", "includes," and "included," is not limiting. The use of the term "having" as well as other forms, such as "have", "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

Where a range of values is provided, it is understood that the upper and lower limit, and each intervening value between the upper and lower limit of the range is encompassed within the embodiments.

As used herein, the term "wt. %" refers to percentage by weight.

It is to be understood that certain radical naming conventions can include either a mono-radical or a di-radical, depending on the context. For example, where a substituent requires two points of attachment to the rest of the molecule, it is understood that the substituent is a di-radical. For example, a substituent identified as alkyl that requires two points of attachment includes di-radicals such as —$CH_2$—, —$CH_2CH_2$—, —$CH_2CH(CH_3)CH_2$—, and the like. Other radical naming conventions clearly indicate that the radical is a di-radical such as "alkylene" or "alkenylene."

As used herein, "$C_a$ to $C_b$" in which "a" and "b" are integers refer to the number of carbon atoms in an alkyl, alkenyl or alkynyl group, or the number of ring atoms of a cycloalkyl or aryl group. That is, the alkyl, the alkenyl, the alkynyl, the ring of the cycloalkyl, and ring of the aryl can contain from "a" to "b", inclusive, carbon atoms. For example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—; a $C_3$ to $C_4$ cycloalkyl group refers to all cycloalkyl groups having from 3 to 4 carbon atoms, that is, cyclopropyl and cyclobutyl. Similarly, a "4 to 6 membered heterocyclyl" group refers to all heterocyclyl groups with 4 to 6 total ring atoms, for example, azetidine, oxetane, oxazoline, pyrrolidine, piperidine, piperazine, morpholine, and the like. If no "a" and "b" are designated with regard to an alkyl, alkenyl, alkynyl, cycloalkyl, or aryl group, the broadest range described in these definitions is to be assumed. As used herein, the term "$C_1$-$C_{22}$" includes $C_1$, $C_2$, $C_3$, $C_4$, $C_5$, $C_6$, $C_7$, $C_8$, $C_9$, $C_{10}$, $C_{11}$, $C_{12}$, up to $C_{22}$, and a range defined by any of the two numbers.

As used herein, "alkyl" refers to a straight or branched hydrocarbon chain that is fully saturated (i.e., contains no double or triple bonds). The alkyl group may have 1 to 22 carbon atoms (whenever it appears herein, a numerical range such as "1 to 22" refers to each integer in the given range; e.g., "1 to 22 carbon atoms" means that the alkyl group may consist of 1 carbon atom, 2 carbon atoms, 3 carbon atoms, etc., up to and including 22 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 6 carbon atoms. The alkyl group may be designated as "$C_1$-$C_4$ alkyl" or similar designations. By way of example only, "$C_1$-$C_6$ alkyl" indicates that there are one to six carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkoxy" refers to the formula —OR wherein R is an alkyl as is defined above, such as "$C_1$-$C_9$ alkoxy", including but not limited to methoxy, ethoxy, n-propoxy, 1-methylethoxy (isopropoxy), n-butoxy, iso-butoxy, sec-butoxy, and tert-butoxy, and the like.

As used herein, "alkenyl" refers to a straight or branched hydrocarbon chain containing one or more double bonds. The alkenyl group may have 2 to 22 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 6 carbon atoms. The alkenyl group may be designated as "$C_2$-$C_6$ alkenyl" or similar designations. By way of example only, "$C_2$-$C_6$ alkenyl" indicates that there are two to six carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4- yl. Typical alkenyl groups include, but are in no way limited to, ethenyl, propenyl, butenyl, pentenyl, and hexenyl, and the like.

As used herein, "alkynyl" refers to a straight or branched hydrocarbon chain containing one or more triple bonds. The alkynyl group may have 2 to 22 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 6 carbon atoms. The alkynyl group may be designated as "$C_2$-$C_6$ alkynyl" or similar designations. By way of example only, "$C_2$-$C_6$ alkynyl" indicates that there are two to six carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

The term "aromatic" refers to a ring or ring system having a conjugated pi electron system and includes both carbocyclic aromatic (e.g., phenyl) and heterocyclic aromatic groups (e.g., pyridine). The term includes monocyclic or fused-ring polycyclic (i.e., rings which share adjacent pairs of atoms) groups provided that the entire ring system is aromatic.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some embodiments, the aryl group has 6 to 10 carbon atoms. The aryl group may be designated as "$C_6$-$C_{10}$ aryl," "$C_6$ or $C_{10}$ aryl," or similar designations. Examples of aryl groups include, but are not limited to, phenyl, naphthyl, azulenyl, and anthracenyl.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some embodiments, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation provided that at least one ring in a ring system is not aromatic. Thus, carbocyclyls include cycloalkyls, cycloalkenyls, and cycloalkynyls. The carbocyclyl group may have 3 to 20 carbon atoms, although the present definition also covers the occurrence of the term "carbocyclyl" where no numerical range is designated. The carbocyclyl group may also be a medium size carbocyclyl having 3 to 10 carbon atoms. The carbocyclyl group could also be a carbocyclyl having 3 to 6 carbon atoms. The carbocyclyl group may be designated as "$C_3$-$C_6$ carbocyclyl" or similar designations. Examples of carbocyclyl rings include, but are not limited to, cyclopropyl, cyclobutyl, cyclopentyl, cyclohexyl, cyclohexenyl, 2,3-dihydro-indene, bicycle[2.2.2] octanyl, adamantyl, and spiro[4.4]nonanyl.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. The heteroatom(s) may be present in either a non-aromatic or aromatic ring in the ring system. The heterocyclyl group may have 3 to 20 ring members (i.e., the number of atoms making up the ring backbone, including carbon atoms and heteroatoms), although the present definition also covers the occurrence of the term "heterocyclyl" where no numerical range is designated. The heterocyclyl group may also be a medium size heterocyclyl having 3 to 10 ring members. The heterocyclyl group could also be a heterocyclyl having 3 to 6 ring members. The heterocyclyl group may be designated as "3-6 membered heterocyclyl" or similar designations. In preferred six membered monocyclic heterocyclyls, the heteroatom(s) are selected from one up to three of O, N or S, and in preferred five membered monocyclic heterocyclyls, the heteroatom(s) are selected from one or two heteroatoms selected from O, N, or S. Examples of heterocyclyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, "cycloalkyl" means a fully saturated carbocyclyl ring or ring system. Examples include cyclopropyl, cyclobutyl, cyclopentyl, and cyclohexyl.

As used herein, "alkoxyalkyl" or "(alkoxy)alkyl" refers to an alkoxy group connected via an alkylene group, such as $C_2$-$C_8$ alkoxyalkyl, or ($C_1$-$C_6$ alkoxy)$C_1$-$C_6$ alkyl, for example, —$(CH_2)_{1-3}$—$OCH_3$.

When a group is described as "optionally substituted" it may be either unsubstituted or substituted. Likewise, when a group is described as being "substituted", the substituent may be selected from one or more of the indicated substituents. As used herein, a substituted group is derived from the unsubstituted parent group in which there has been an exchange of one or more hydrogen atoms for another atom or group. Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$ carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 3-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), (aryl)$C_1$-$C_6$ alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), (5-10 membered heteroaryl)$C_1$-$C_6$ alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, —CN, hydroxy, $C_1$-$C_6$ alkoxy, ($C_1$-$C_6$ alkoxy)$C_1$-$C_6$ alkyl, —O($C_1$-$C_6$ alkoxy)$C_1$-$C_6$ alkyl; ($C_1$-$C_6$ haloalkoxy)$C_1$-$C_6$ alkyl; —O($C_1$-$C_6$ haloalkoxy)$C_1$-$C_6$ alkyl; aryloxy, sulfhydryl (mercapto), halo($C_1$-$C_6$)alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, —$SO_3H$, sulfino, —$OSO_2C_{1-4}$ alkyl, and oxo (=O). Wherever a group is described as "optionally substituted" that group can be substituted with the above substituents.

The term "hair" refers to one or more than one strands of hair, as well as the natural components of hair, such as oil from a body. Hair may refer to virgin hair or processed hair, for example hair that has been exposed to hair waving or hair straightening formulations.

The term "untreated hair" refers to virgin hair, or refers to hair that has been treated with a hair treatment formulation (e.g. a bleaching or a coloring formulation) that does not contain one or more diester compounds described herein (e.g. a compound of Formula (I) or Formula (II)).

The term "shampoo" generally refers to a liquid or semi-solid formulation applied to the hair that contains detergent or soap for washing the hair.

The term "conditioner" generally refers to a formulation (e.g., liquid, cream, lotion, gel, semi-solid) applied to the hair to soften the hair, smooth the hair, and/or change the sheen of the hair.

Diester Compounds

Some embodiments described herein generally relate to a compound of Formula (I) or Formula (II), or a combination thereof, having the structure:

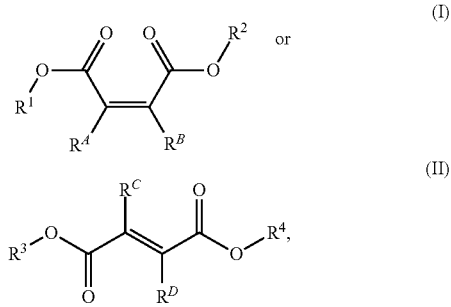

wherein: each of $R^1$, $R^2$, $R^3$ and $R^4$ is independently selected from the group consisting of an optionally substituted $C_1$-$C_{22}$ alkyl, an optionally substituted $C_2$-$C_{22}$ alkenyl, an optionally substituted $C_2$-$C_{22}$ alkynyl, an optionally substituted $C_3$-$C_{10}$ carbocyclyl, an optionally substituted $C_6$-$C_{10}$ aryl, an optionally substituted 5 to 10 membered heteroaryl, an optionally substituted 3 to 10 membered heterocyclyl, and an optionally substituted $C_2$-$C_{22}$ alkoxyalkyl; and each of $R^A$, $R^B$, $R^C$ and $R^D$ is independently hydrogen or an optionally substituted $C_1$-$C_{22}$ alkyl.

In some embodiments, the compound can be a compound of Formula (I), where each of $R^1$ and $R^2$ is independently selected from the group consisting of an optionally substituted $C_1$-$C_{22}$ alkyl, an optionally substituted $C_2$-$C_{22}$ alkenyl, an optionally substituted $C_2$-$C_{22}$ alkynyl, an optionally substituted $C_3$-$C_{10}$ carbocyclyl, an optionally substituted $C_6$-$C_{10}$ aryl, an optionally substituted 5 to 10 membered heteroaryl, an optionally substituted 3 to 10 membered heterocyclyl, and an optionally substituted $C_2$-$C_{22}$ alkoxyalkyl; and each of $R^A$ and $R^B$ is independently hydrogen or an optionally substituted $C_1$-$C_{22}$ alkyl. For example, in some embodiments, each of $R^1$ and $R^2$ is independently selected from the group consisting of an optionally substituted $C_8$ alkyl; and each of $R^A$ and $R^B$ is hydrogen.

In some embodiments of the compound of Formula (I), each of $R^1$ and $R^2$ is independently an unsubstituted $C_1$-$C_{22}$ alkyl (e.g., unsubstituted $C_1$-$C_6$ alkyl or unsubstituted $C_7$-$C_{12}$ alkyl). In some embodiments, each of $R^1$ and $R^2$ is independently an unsubstituted $C_2$-$C_{22}$ alkenyl (e.g., unsubstituted $C_2$-$C_6$ alkenyl or unsubstituted $C_7$-$C_{12}$ alkenyl). In some embodiments, each of $R^1$ and $R^2$ is independently an unsubstituted $C_2$-$C_{22}$ alkynyl (e.g., unsubstituted $C_2$-$C_6$ alkynyl or unsubstituted $C_7$-$C_{12}$ alkynyl). In some embodiments, each of $R^1$ and $R^2$ is independently an unsubstituted $C_3$-$C_{10}$ carbocyclyl (e.g., unsubstituted $C_3$-$C_6$ cycloalkyl). In some embodiments, each of $R^1$ and $R^2$ is independently an unsubstituted $C_6$-$C_{10}$ aryl (e.g., unsubstituted phenyl). In some embodiments, each of $R^1$ and $R^2$ is independently an unsubstituted 5 to 10 membered heteroaryl (e.g., unsubstituted 5 or 6 membered heteroaryl containing 1 to 3 heteroatoms selected from the group consisting of N, O and S). In some embodiments, each of $R^1$ and $R^2$ is independently an unsubstituted 3 to 10 membered heterocyclyl (e.g., unsubstituted 3 to 6 membered heterocyclyl containing 1 to 3 heteroatoms selected from the group consisting of N, O and S). In some embodiments, each of $R^1$ and $R^2$ is independently an unsubstituted $C_2$-$C_{22}$ alkoxyalkyl (e.g., unsubstituted ($C_1$-$C_6$ alkoxy)$C_1$-$C_6$ alkyl). In some embodiments, $R^1$ is a substituted $C_1$-$C_{22}$ alkyl. In some embodiments, each of $R^1$ and $R^2$ is independently a substituted $C_2$-$C_{22}$ alkenyl. In some embodiments, each of $R^1$ and $R^2$ is independently a substituted $C_2$-$C_{22}$ alkynyl. In some embodiments, each of $R^1$ and $R^2$ is independently a substituted $C_3$-$C_{10}$ carbocyclyl. In some embodiments, each of $R^1$ and $R^2$ is independently a substituted $C_6$-$C_{10}$ aryl. In some embodiments, each of $R^1$ and $R^2$ is independently a substituted 5 to 10 membered heteroaryl. In some embodiments, each of $R^1$ and $R^2$ is independently a substituted 3 to 10 membered heterocyclyl. In some embodiments, each of $R^1$ and $R^2$ is independently a substituted $C_2$-$C_{22}$ alkoxyalkyl.

In some embodiments of the compound of Formula (I), $R^A$ is hydrogen. In some embodiments, $R^A$ is an unsubstituted $C_1$-$C_{22}$ alkyl. In some embodiments, $R^A$ is a substituted $C_1$-$C_{22}$ alkyl. In some embodiments, $R^B$ is hydrogen. In some embodiments, $R^B$ is an unsubstituted $C_1$-$C_{22}$ alkyl. In some embodiments, $R^B$ is a substituted $C_1$-$C_{22}$ alkyl.

In some further embodiments of the compound of Formula (I), each of $R^1$ and $R^2$ is independently an unsubstituted $C_1$-$C_6$ alkyl (e.g., methyl, ethyl, propyl, isopropyl, n-butyl, isobutyl, t-butyl, n-pentyl, isopentyl, n-hexyl, isohexyl), and each of $R^A$ and $R^B$ is hydrogen. In one embodiment, each of $R^1$ and $R^2$ is n-butyl. In some other embodiments, each of $R^1$ and $R^2$ is independently an unsubstituted $C_7$-$C_{12}$ alkyl (e.g., n-heptyl, iso-heptyl, n-octyl, iso-octyl, ethylhexyl, 2-ethylhexyl, n-nonyl, isononyl, n-decyl, iso-decyl, ethyloctyl), and each of $R^A$ and $R^B$ is hydrogen. In some additional embodiments of the compound of Formula (I), each of $R^1$ and $R^2$ is independently an optionally substituted $C_8$ alkyl, and each of $R^A$ and $R^B$ is hydrogen. In one embodiment, each of $R^1$ and $R^2$ is n-octyl, and the compound of Formula (I) is dioctyl maleate. In another embodiment, each of $R^1$ and $R^2$ is ethylhexyl (e.g., 2-ethylhexyl), and the compound of Formula (I) is bis(2-ethylhexyl)maleate.

In some embodiments, the compound can be a compound of Formula (II), where each of $R^3$ and $R^4$ is independently selected from the group consisting of an optionally substituted $C_1$-$C_{22}$ alkyl, an optionally substituted $C_2$-$C_{22}$ alkenyl, an optionally substituted $C_2$-$C_{22}$ alkynyl, an optionally substituted $C_3$-$C_{10}$ carbocyclyl, an optionally substituted $C_6$-$C_{10}$ aryl, an optionally substituted 5 to 10 membered heteroaryl, an optionally substituted 3 to 10 membered heterocyclyl, and an optionally substituted $C_2$-$C_{22}$ alkoxyalkyl; and each of $R^C$ and $R^D$ is independently hydrogen or an optionally substituted $C_1$-$C_{22}$ alkyl.

In some embodiments of the compound of Formula (II), each of $R^3$ and $R^4$ is independently an unsubstituted $C_1$-$C_{22}$ alkyl (e.g., unsubstituted $C_1$-$C_6$ alkyl or unsubstituted $C_7$-$C_{12}$ alkyl). In some embodiments, each of $R^3$ and $R^4$ is independently an unsubstituted $C_2$-$C_{22}$ alkenyl (e.g., unsubstituted $C_2$-$C_6$ alkenyl or unsubstituted $C_7$-$C_{12}$ alkenyl). In some embodiments, each of $R^3$ and $R^4$ is independently an unsubstituted $C_2$-$C_{22}$ alkynyl (e.g., unsubstituted $C_2$-$C_6$ alkynyl or unsubstituted $C_7$-$C_{12}$ alkynyl). In some embodiments, each of $R^3$ and $R^4$ is independently an unsubstituted $C_3$-$C_{10}$ carbocyclyl (e.g., unsubstituted $C_3$-$C_6$ cycloalkyl). In some embodiments, each of $R^3$ and $R^4$ is independently an unsubstituted $C_6$-$C_{10}$ aryl (e.g., unsubstituted phenyl). In some embodiments, each of $R^3$ and $R^4$ is independently an unsubstituted 5 to 10 membered heteroaryl (e.g., unsubstituted 5 or 6 membered heteroaryl containing 1 to 3 heteroatoms selected from the group consisting of N, O and S). In some embodiments, each of $R^3$ and $R^4$ is independently an unsubstituted 3 to 10 membered heterocyclyl (e.g., unsubstituted 3 to 6 membered heterocyclyl containing 1 to 3 heteroatoms selected from the group consisting of N, O and S). In some embodiments, each of $R^3$ and $R^4$ is independently an unsubstituted $C_2$-$C_{22}$ alkoxyalkyl (e.g., unsubstituted $C_1$-$C_6$ alkoxy)$C_1$-$C_6$ alkyl). In some embodiments, each of $R^3$ and $R^4$ is independently a substituted $C_1$-$C_{22}$ alkyl. In some embodiments, each of $R^3$ and $R^4$ is independently a substituted $C_2$-$C_{22}$ alkenyl. In some embodiments, each of $R^3$ and $R^4$ is independently a substituted $C_2$-$C_{22}$ alkynyl. In some embodiments, each of $R^3$ and $R^4$ is independently a substituted $C_3$-$C_{10}$ carbocyclyl. In some embodiments, each of $R^3$ and $R^4$ is independently a substituted $C_6$-$C_{10}$ aryl. In some embodiments, each of $R^3$ and $R^4$ is independently a substituted 5 to 10 membered heteroaryl. In some embodiments, each of $R^3$ and $R^4$ is independently a substituted 3 to 10 membered heterocyclyl. In some embodiments, each of $R^3$ and $R^4$ is independently a substituted $C_2$-$C_{22}$ alkoxyalkyl.

In some embodiments of the compound of Formula (II), $R^C$ is hydrogen. In some embodiments, $R^C$ is an unsubstituted $C_1$-$C_{22}$ alkyl. In some embodiments, $R^C$ is a substituted $C_1$-$C_{22}$ alkyl. In some embodiments, $R^D$ is hydrogen. In some embodiments, $R^D$ is an unsubstituted $C_1$-$C_{22}$ alkyl. In some embodiments, $R^D$ is a substituted $C_1$-$C_{22}$ alkyl.

In some further embodiments of the compound of Formula (II), each of $R^3$ and $R^4$ is independently an unsubstituted $C_1$-$C_6$ alkyl (e.g., methyl, ethyl, propyl, isopropyl, n-butyl, isobutyl, t-butyl, n-pentyl, isopentyl, n-hexyl, isohexyl), and each of $R^C$ and $R^D$ is hydrogen. In one embodiment, each of $R^1$ and $R^2$ is n-butyl. In some further embodiments, each of $R^3$ and $R^4$ is independently an unsubstituted $C_7$-$C_{12}$ alkyl (e.g., n-heptyl, iso-heptyl, n-octyl, iso-octyl, ethylhexyl, 2-ethylhexyl, n-nonyl, isononyl, n-decyl, iso-decyl, ethyloctyl), and each of $R^C$ and $R^D$ is hydrogen. In some additional embodiments, each of $R^3$ and $R^4$ is independently an optionally substituted $C_8$ alkyl, and each of $R^C$ and $R^D$ is hydrogen. In one embodiment, each of $R^3$ and $R^4$ is n-octyl. In another embodiment, each of $R^3$ and $R^4$ is ethylhexyl (e.g., 2-ethylhexyl).

Cosmetic Formulations

Some embodiments described herein relate to a cosmetic formulation that can include an effective amount of one or more compounds described herein, for example a compound of Formulae (I) or Formula (II) or a combination thereof (i.e., the active ingredient) as described herein, and one or more cosmetically acceptable carriers or excipients. In some embodiments, the cosmetic formulation is a hair treatment formulation, a skin treatment formulation, a nail treatment formulation, or combinations thereof.

In some embodiments, the cosmetic formulation comprises, comprises about, comprises at least, or comprises at least about, 0.05 wt. %, 0.1 wt. %, 0.5 wt. %, 1 wt. %, 2 wt. %, 3 wt. %, 5 wt. %, 10 wt. %, 15 wt. %, 20 wt. %, 25 wt. %, 30 wt. %, 35 wt. %, 40 wt. %, 45 wt. %, 50 wt. %, 60 wt. %, 65 wt. %, 70 wt. %, or 75 wt. % of the one or more compounds of Formula (I) or (II), or a range defined by any two of the preceding values. In some embodiments, the cosmetic formulation comprises, comprises about, comprises at least, or comprises at least about, 1 wt. %, 2 wt. %, 3 wt. %, 5 wt. %, 10 wt. %, 15 wt. %, 20 wt. %, 25 wt. %, 30 wt. %, 35 wt. %, 40 wt. %, 45 wt. %, 50 wt. %, 55 wt. %, 60 wt. %, 65 wt. %, 70 wt. %, 75 wt. % or 80 wt. % of the one or more compounds of Formula (I) or (II), or a range defined by any two of the preceding values, when applied to coarse hair (e.g. African American hair) and/or hair subjected to repeated damage caused by bleaching, coloring, perming, relaxing, straightening, heat styling, etc.).

In some embodiments, cosmetically acceptable carrier comprises water, ethyl acetate, acetone, alcohol, polyol, oil, silicone, liposomes, or ester, or combinations thereof. In some embodiments, the polyol is glycol, such as ethylene glycol or propylene glycol. In some embodiments, the water is purified water, distilled water, deionized water, or combinations thereof. In some embodiments, the cosmetic formulation comprises, comprises about, comprises at least, or comprises at least about, 5 wt. %, 10 wt. %, 15 wt. %, 20 wt. %, 25 wt. %, 30 wt. %, 35 wt. %, 40 wt. %, 45 wt. %, 50 wt. %, 60 wt. %, 65 wt. %, 70 wt. %, 75 wt. %, 80 wt. %, 85 wt. %, 90 wt. %, 95 wt. %, 98 wt. % or 99 wt. % of a cosmetically acceptable carrier, or a range defined by any two of the preceding values, such as water.

In some embodiments, the cosmetically acceptable excipient comprises a surfactant, a vitamin, a natural extract, a preservative, an antioxidant, a chelating agent, a protein, an amino acid, a humectant, a fragrance, an emollient, a penetrant, a thickener, a viscosity modifier, a hair fixative, a film former, an emulsifier, an opacifying agent, a propellant, a carrier, a salt, a buffer, an anti-static agent, an anti-frizz agent, an anti-dandruff agent, or a colorant, or combinations thereof. The cosmetically acceptable excipient is typically present in an amount ranging from about 10 wt. % to about 99.99 wt. % of the cosmetic formulation, for example, from about 40 wt. % to about 99 wt. %, or from about 80 wt. % to about to about 99 wt. %.

In some embodiments, the cosmetic formulation is in the form of a gel, liquid, cream, powder, lotion, milk, mousse, spray, shampoo, conditioner, and the like.

In some embodiments, the cosmetic formulation further comprises a pH modifying agent. In some embodiments, the cosmetic formulation further comprises one or more hair treatment agents. In some embodiments, the one or more hair treatment agents comprises a bleaching agent, a relaxing agent, a coloring agent, a shampooing agent, or a conditioning agent, or combinations thereof. In some embodiments, the bleaching agent comprises one or more persulfate salts, or hydrogen peroxide, or a combination thereof. In some embodiments, the persulfate salt is potassium persulfate, ammonium persulfate, or sodium persulfate, or combinations thereof. In some embodiments, the hydrogen peroxide has a pH of at least about 10. In some embodiments, the hydrogen peroxide has a pH of at least about 3. In some embodiments, the relaxing agent comprises sodium hydroxide, lithium hydroxide, potassium hydroxide, guanidinium hydroxide, ammonium hydroxide, a sulfite salt, or a thioglycolate salt, or combinations thereof. In some embodiments, the sulfite salt is sodium sulfite or potassium sulfite or a combination thereof. In some embodiments, the coloring agent is one or more oxidative dyes, direct dyes, natural dyes, metallic dyes, reactive dyes or combinations thereof. In some embodiments, oxidative dyes are selected from one or more oxidation bases. In some embodiments, the oxidation base is selected from one or more para-phenylenediamines, bis(phenyl)alkylenediamines, para-aminophenols, ortho-aminophenols, heterocyclic bases (e.g. pyridine derivatives, pyrimidine derivatives and pyrazole derivatives), the addition salts thereof, the substituted analogs, and combinations thereof. In some embodiments, the oxidative dye further comprises one or more couplers. In some embodiments, the coupler is selected from one or more meta-phenylenediamines, meta-aminophenols, meta-diphenols, naphthalene-based couplers, heterocyclic couplers, the addition salts thereof, and combinations thereof. In some embodiments, addition salts of the oxidation bases and couplers may be addition salts with an acid such as the hydrochlorides, hydrobromides, sulfates, citrates, succinates, tartrates, lactates, tosylates, benzenesulfonates, phosphates and acetates. In some embodiments, the direct dye includes one or more of a synthetic dye, a natural dye, or combinations thereof. In some embodiments, the direct dye includes one or more cationic dyes, anionic dyes, nonionic dyes, or combinations thereof. In some embodiments, the direct dye is selected from one or more azo dyes, diazo dyes, (poly)methine dyes (e.g. cyanins, hemicyanins and styryls), carbonyl dyes, azine dyes, nitro(hetero)aryl dyes, tri(hetero) arylmethane dyes, porphyrin dyes, phthalocyanin dyes, and natural dyes, hydrazono dyes. In some embodiments, the natural dye is selected from one or more of lawsone, juglone, alizarin, purpurin, carminic acid, kermesic acid, purpurogallin, protocatechaldehyde, indigo, isatin, curcumin, spinulosin, apigenidin, orceins, extracts thereof, decoctions thereof, and combinations thereof. In some embodiments, the cosmetic formulation does not or does not substantially comprise a coloring agent and/or a dye (e.g. an oxidative dye and/or a direct dye). In some embodiments, the cosmetic formulation further comprises a product colorant or pigment (e.g. food color) for the purpose of modifying the aesthetic color of the cosmetic formulation.

A particular embodiment of the cosmetic formulation described herein is a hair bleaching formulation comprising: about 1% wt. to about 12% wt. of hydrogen peroxide; about 10% wt. to about 40% wt. of one or more persulfate salts; and about 0.5% wt. to about 20 wt. %, or about 1 wt. % to about 10 wt. % of a compound of Formula (I) or (II) or a combination thereof. In some further embodiments, the cosmetic formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof. The hair bleaching formulation may also comprise one or more cosmetically acceptable excipients and carrier as described herein.

Another embodiment of the cosmetic formulation described herein is cosmetic formulation is in the form of a colorless nail base or primer, which is applied as a base coat prior to the application of one or more nail polish containing coloring agents. The nail base or primer may comprise about 1% to about 60%, about 2% to about 50%, or about 5% to about 30% by weight of a compound of Formula (I) or (II) or a combination thereof, and one or more volatile solvents. In some further embodiments, the cosmetic formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof. The nail base or primer may also comprise one or more cosmetically acceptable excipients and carrier as described herein.

Humectants

Humectant is a substance that attracts and retains moisture. Humectants used in cosmetic and personal care products and compositions include synthetic humectants (such as propylene glycol, urea, polyethylene glycol (PEG) and natural humectants (such as sugars, betains, amino acids, honey, aloe extract, hyaluronic acid, and glycerin. In one particular example, the humectant may include glycine betaine (*Beta vulgaris*), which is a beet sugar extract. Unlike traditional humectants, which draw moisture from the environment, glycine betaine adds hydration directly due to its abundant source of saccharides. One or more humectants may be included in the cosmetic or personal care formulation described herein, in an amount ranging from about 0.1 wt. % to about 15% wt. the formulation, or from about 0.5% wt. to about 10% wt. of the formulation, or from about 1% to about 5% of the formulation.

Emollients

Emollient is a substance that protects against wetness or irritation, softens, soothes, coats, lubricates, moisturizes, protects, and/or cleanses the skin. Suitable emollients for use in the cosmetic formulations include, but are not limited to, a silicone compound (e.g., dimethicone, cyclomethicone, dimethicone copolyol or a mixture of cyclopentasiloxane and dimethicone/vinyldimethicone cross polymer, cyclopentasiloxane polysilicone), polyols such as sorbitol, glycerin, propylene glycol, ethylene glycol, polyethylene glycol, caprylyl glycol, polypropylene glycol, 1,3-butane diol, hexylene glycol, isoprene glycol, xylitol; ethylhexyl palmitate; a triglyceride such as caprylic/capric triglyceride and fatty acid ester such as cetearyl isononanoate or cetyl palmitate. In a specific embodiment, the emollient is dimethicone, amidodimethicone, dimethiconol, cyclopentasiloxane, potassium dimethicone PEG-7 panthenyl phosphate, or combinations thereof. More than one emollient may be included in the cosmetic or personal care formulation described herein, in an amount ranging from about 0.1 wt. % to about 15% wt. the formulation, or from about 0.5% wt. to about 10% wt. of the formulation, or from about 1% to about 5% of the formulation.

Emulsifiers

The formulation may also contain one or more emulsifiers. Suitable emulsifiers include, but are not limited to, copolymers of an unsaturated ester and styrene sulfonate monomer, cetearyl alcohol, glyceryl ester, polyoxyethylene glycol ether of cetearyl alcohol, stearic acid, polysorbate-20, ceteareth-20, lecithin, glycol stearate, polysorbate-60, polysorbate-80, or combinations thereof. More than one emulsifier may be included in the formulation in the cosmetic or personal care formulation described herein, in an amount ranging from about 0.05 wt. % to about 15% wt. the formulation, or from about 0.1% wt. to about 10% wt. of the formulation, or from about 0.5% to about 5% of the formulation.

Surfactants and Solubilizers

In some embodiments, the cosmetic or personal care formulations may further comprise one or more surfactants, or solubilizer, or combinations thereof.

Solubilizers, as used herein, refers to a compound that can help to make otherwise insoluble liquids soluble in water. For example, essential oils do not mix well with water. Mixing essential oils with a solubilizer before adding to water will help the essential oil mix well with water. Examples of solubilizers include polysorbates, safflower oleosomes, and propanediol.

Surfactants are surface-active agents that are able to reduce the surface tension of water and cause the hair formulation to slip across or onto the skin or hair. Surfactants also include detergents and soap. The surfactants may be amphoteric, anionic, or cationic. Suitable surfactants that may be used in the formulation include, but are not limited to, 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium C12-15 alkyl sulfate, ammonium C12-15 pareth sulfate, ammonium C12-16 alkyl sulfate, ammonium C9-10 perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, behenalkonium chloride, behenamide, behenamide, behenamidopropyl betaine, behenamine oxide, sodium laureth sulfate, sodium lauryl sulfate, a polyoxyether of lauryl alcohol or ceteareth-20, or combinations thereof.

Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, behentrimonium chloride, behentrimonium methosulfate, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

In some embodiments, the surfactants that may be used in the present invention are natural surface active agents, such as saponin, lecithin, soybean phospholipid, hydrogenated soybean phospholipid, soybean lysophospholipid, hydrogenated soybean lysophospholipid, egg yolk lecithin, hydrogenated egg yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid, mannosyl erythritol lipid, surfactin and its salts.

More than one surfactant may be included in the formulation. In some embodiments, the cosmetic or personal care formulation described herein comprises one or more surfactants in an amount ranging from about 0.1 wt. % to about 15% wt. the formulation, or from about 0.5% wt. to about 10% wt. of the formulation, or from about 1% to about 5% of the formulation.

Essential Oils

Various essential oils may be used in the cosmetic or personal care formulations described herein. Essential oils may act as a fragrance, or may also confer additional benefits due to the nature of the essential oils, including but not limited to cleansing, nourishing, and strengthening the hair follicles and shaft. However, most essential oils are highly concentrated and potent, and they may have adverse effect on skin if used undiluted. In certain hair and skin care products, essential oils are diluted with carrier oils. Carrier oils are a vegetable origin extracted from nuts and seeds by cold pressing. Carrier oils provide lubrication and moisture and help with the absorption of essential oils into the skin. In some embodiments of the cosmetic formulation described herein, the one or more essential oils are used without any carrier oil. In some embodiments, the cosmetic formulation comprises about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1.0%, 1.5%, 2.0%, 2.5%, 3.0%, 3.5%, 4.0%, 4.5%, or 5.0% by weight essential oils, or a range defined by any two preceding values.

Non-limiting embodiments of the essential oils that may be used in the present invention are described herein. In some embodiments, the one or more essential oils are selected from the group consisting of lavender oil, tea tree oil, peppermint oil, rosemary oil, and combinations thereof. Other essential oils that may be used in the present invention include, but are not limited to, allspice berry essential oil, angelica seed essential oil, anise seed essential oil, basil essential oil, bay laurel essential oil, bay essential oil, bergamot essential oil, blood orange essential oil, camphor essential oil, caraway seed essential oil, cardamom seed essential oil, carrot seed essential oil, cassia essential oil, catnip essential oil, cedarwood essential oil, celery seed essential oil, chamomile essential oil, chamomile roman essential oil, cinnamon bark essential oil, cinnamon leaf essential oil, citronella essential oil, clary sage essential oil, clove bud essential oil, coriander seed essential oil, cypress essential oil, elemi essential oil, eucalyptus essential oil, fennel essential oil, fir needle essential oil, frankincense essential oil, geranium essential oil, ginger essential oil, grapefruit essential oil, helichrysum essential oil, hop essential oil, hyssop essential oil, juniper berry essential oil, labdanum essential oil, lemon essential oil, lemongrass essential oil, lime essential oil, magnolia essential oil, mandarin essential oil, marjoram essential oil, myrrh essential oil, myrtle essential oil, neroli essential oil, niaouli essential oil, nutmeg essential oil, orange essential oil, oregano essential oil, palmarosa essential oil, patchouli essential oil, pennyroyal essential oil, pepper black essential oil, petitgrain essential oil, pine needle essential oil, radiata essential oil, ravensara essential oil, rose essential oil, rosewood essential oil, sage essential oil, sandalwood essential oil, spearmint essential oil, spikenard essential oil, spruce essential oil, star anise essential oil, tangerine essential oil, thyme red essential oil, verbena essential oil, vetiver essential oil, wintergreen essential oil, wormwood essential oil, yarrow essential oil, or Ylang Ylang Extra essential oil, or combinations thereof.

Hydrocarbons

In some instances, the cosmetic or personal care formulations described herein may also contain hydrocarbons, fat, oil, or wax that are not volatile (as in contrast to the essential oils, which are very volatile). In some embodiments, the hydrocarbons may include ozokerite, α-olefin oligomer, light isoparaffin, light liquid isoparaffin, squalene, squalane, vegetable squalane, ceresin, paraffin, polyethylene powder, polybutene, microcrystalline wax, liquid isoparaffin, liquid paraffin, mineral oil and vaseline.

Fat/Wax/Non-Volatile Oil

Natural fats, wax and oils that may be suitable for the present invention include but not limited to jojoba oil, carnauba wax, candelilla wax, rice wax, shellac, lanoline, mink tallow wax, spermaceti, sugar cane wax, sperm whale oil, beeswax and montan wax, argan oil, avocado oil, almond oil, olive oil, extra virgin olive oil, sesame oil, rice bran oil, rice oil, rice germ oil, corn oil, soybean oil, corn oil, persic oil, palm kernel oil, palm oil, castor oil, grape seed oil, cottonseed oil, coconut oil, hydrogenated coconut oil, beef tallow, hydrogenated oil, horse oil, mink oil, egg yolk oil, egg yolk fatty oil, rose hips oil, candlenut oil, wheat germ oil, peanut oil, camellia oil, sasanqua oil, cacao butter, Japan wax, beef bone fat, beef foot oil, hog fat, horse fat, mutton tallow, shea butter, macadamia nut oil and meadowfoam seed oil.

Viscosity Modifying Agents

The cosmetic or personal care formulations may contain one or more viscosity modifying agents, such as viscosity increasing agents. Classes of such agents include, but are not limited to, viscous liquids, such as polyethylene glycol, semisythetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof.

Antioxidants

The cosmetic or personal care formulation may contain one or more antioxidants. Examples include, but are not limited to, tocopheryls, BHT, ascorbic acid, *Camellia sinensis* leaf extract, ascorbyl palmitate, magnesium ascorbyl phosphate, carotenoids, resveratrol, triethyl citrate, arbutin, kojic acid, tetrahexydecyl ascorbate, superoxide dismutase, zinc, sodium metabisulfite, lycopene, ubiquinone, and combinations thereof.

Opacifying Agents

The cosmetic or personal care formulation may contain one or more opacifying agents. Opacifying agents are added to the formulations to make it opaque. Suitable opacifying agents include, but are not limited to, glycol distearate and ethoxylated fatty alcohols.

Ultraviolet Absorbing Agents

In some embodiments, the cosmetic formulation may include at least one ultraviolet absorbing agent. Non-limiting examples include p-aminobenzoic acid, p-aminobenzoic acid derivatives, such as ethyl p-aminobenzoate, glyceryl p-aminobenzoate, amyl p-dimethylaminobenzoate and 2-ethylhexyl p-dimethylaminobenzoate, cinnamic acid derivatives, such as benzyl cinnamate, glyceryl di-p-methoxycinnamate mono-2-ethylhexanoate, methyl 2,4-diisopropylcinnamate, ethyl 2,4-diisopropylcinnamate, potassium p-methoxycinnamate, sodium p-methoxycinnamate, isopropyl p-methoxycinnamate, 2-ethylhexyl p-methoxycinnamate, 2-ethoxyethyl p-methoxycinnamate and ethyl p-ethoxycinnamate, urocanic acid, urocanic acid derivatives, such as ethyl urocanate, benzophenone derivatives, such as 2,4-dihydroxybenzophenone, 2,2',4,4'-tetrahydroxybenzophenone, 2-hydroxy-4-methoxy-5-sulfobenzophenone sodium, 2-hydroxy-4-methoxybenzophenone-5-sulfonic acid, 2-hydroxy-4-methoxybenzophenone, 2,2'-dihydroxy-4,4'-dimethoxybenzophenone and 2,2'-dihydroxy-4,4'-dimethoxy-5-sulfobenzophenone sodium, salicylic acid derivatives, such as ethylene glycol salicylate, 2-ethylhexyl salicylate, phenyl salicylate, benzyl salicylate, p-tert-butylphenyl salicylate, homomentyl salicylate and 3,3,5-trimethylcyclohexyl salicylate, 2-(2'-hydroxy-5'-methoxyphenyl)benzotriazole, and 4-tert-butyl-4'-methoxybenzoylmethane.

Preservatives

In some embodiments, the cosmetic formulation is free or essentially free of preservatives. In some other embodiments, the cosmetic composition may comprise one or more preservatives, for example, gluconlactone, sodium benzoate, potassium sorbate, and combinations thereof. Other preservatives that may be used in the present invention include, but are not limited to, benzoic acid, undecylenic acid, salicylic acid, sorbic acid, dehydroacetic acid, sodium dehydroacetate, isobutyl parahydroxybenzoate, isopropyl parahydroxybenzoate, ethyl parahydroxybenzoate, butyl parahydroxybenzoate, propyl parahydroxybenzoate, benzyl parahydroxybenzoate, methyl parahydroxybenzoate, sodium methyl parahydroxybenzoate, and phenoxyethanol.

Other ingredients that may be used in the cosmetic or personal care formulations described herein include, but not limited to pH adjustors, such as citric acid, sodium hydroxide, potassium hydroxide and triethanolamine.

Conditions

The cosmetic or personal care formulations described herein may be in the form of a conditioner. The conditioner typically includes the active agent in a suitable carrier. Additionally, the conditioner may include cationic polymers derived from polysaccharides, for example cationic cellulose derivatives, cationic starch derivatives, cationic guar derivatives and cationic locust bean gum derivatives, synthetic cationic polymers, mixtures or combinations of these agents. The formulation may comprise other synthetic or natural polymers or polymers derived from biological preparation processes, which are functionalized, where appropriate, for example with cationic or neutral groups. These polymers may have a stabilizing or strengthening action on the formulation, and/or a conditioning action (deposition on the surface of the skin or the hair).

The compound of Formula (I) or (II) or a combination thereof as described herein (i.e., the active agent) may be included in any suitable concentration. Typical concentrations of active agent in the conditioner range from small amounts such as at least about 0.01 wt. %, about 0.1 wt. %, and up to about 50 wt. %. Preferably the conditioner contains the active agent in a concentration ranging from 0.1 wt. % to about 10 wt. %, from about 0.5 wt. % to about 8 wt. %, or from about 1 wt. % to about 5 wt. %. While greater concentrations of active agent could be present in the conditioner, they are generally not needed to achieve the desired results.

Shampoos

The cosmetic or personal care formulations described herein may be in the form of a shampoo. The shampoo typically includes the compound of Formula (I) or (II) or a combination thereof as described herein (i.e., the active agent) in a suitable carrier. The active agent may be included in any suitable concentration. Typical concentrations of active agent in the shampoo range from small amounts such as at least about 0.01 wt. %, about 0.1 wt. %, and up to about 50 wt. %. Preferably the conditioner contains the active agent in a concentration ranging from 0.1 wt. % to about 10 wt. %, from about 0.5 wt. % to about 8 wt. %, or from about 1 wt. % to about 5 wt. %. While greater concentrations of active agent could be present in the shampoo, they are generally not needed to achieve the desired results. Additionally, the shampoo may include from about 0.5 wt. % to about 20 wt. % of one or more surfactants, and/or one or more cosmetically acceptable excipients described herein.

Creams, Lotions, Gels, and Polish

The cosmetic or personal care formulations described herein may be in the form of a cream, lotion, gel, or polish. The cream, lotion, gel, or polish typically includes the compound of Formula (I) or (II) or a combination thereof as described herein (i.e., the active agent) in a suitable carrier. The active agent may be included in any suitable concentration. Typical concentrations of active agent in the shampoo range from small amounts such as at least about 0.01 wt. %, about 0.1 wt. %, and up to about 50 wt. %. Preferably the cream, lotion, gel, or polish contains the active agent in a concentration ranging from 0.1 wt. % to about 10 wt. %, from about 0.5 wt. % to about 8 wt. %, or from about 1 wt. % to about 5 wt. %. While greater concentrations of active agent could be present in the cream or lotion, they are generally not needed to achieve the desired results. Additionally, the cream, lotion, gel or polish may comprise one or more cosmetically acceptable excipients described herein.

Sprays

The cosmetic or personal care formulations described herein may be in the form of a spray. The spray typically includes the compound of Formula (I) or (II) or a combination thereof as described herein (i.e., the active agent) and a cosmetically acceptable carrier. Preferably, the active agent in a concentration ranging from 0.1 wt. % to about 10 wt. %, from about 0.5 wt. % to about 8 wt. %, or from about 1 wt. % to about 5 wt. %. In some embodiments, the carrier is water or a water and alcohol mixture. The spray formulation optionally includes an antioxidant, sunscreen agent, vitamin, protein, peptide, plant extract, humectant, oil, emollient, lubricant, thickener, hair conditioning agent, polymer, and/or surfactant. In some embodiments, the spray formulation includes a preservative. In some embodiments, the cosmetic or personal care formulation includes a fragrance. In some embodiments, the formulation includes a surfactant. In some embodiments, the formulation contains water, fragrance, a preservative, and an active agent. In some embodiments, the formulation contains water, fragrance, a preservative, and an active agent. In some embodiments, the formulation contains water, a preservative, fragrance, an active agent, and an anti-static agent. In some embodiments, the formulation contains water, a preservative, fragrance, an active agent, and a hair conditioning agent. In some embodiments, the formulation contains water, a preservative, fragrance, an active agent, and a surfactant.

The spray formulations may be dispensed from containers that include aerosol dispensers or pump spray dispensers. Such dispensers are known in the art and are commercially available from a variety of manufacturers.

Propellants

When the spray formulation is dispensed from a pressurized aerosol container, a propellant may be used to disperse the formulation out of the container. Suitable propellants include, but are not limited to, a liquefiable gas or a halogenated propellant. Examples of suitable propellants include dimethyl ether and hydrocarbon propellants such as propane, n-butane, isobutane, CFCs, and CFC-replacement propellants. The propellants may be used singly or admixed.

The amount of propellant may range from about 10% to about 60% by weight of the formulation. The propellant may be separated from the hair repair formulation as in a two-compartment container. Other suitable aerosol dispensers are those characterized by the propellant being compressed air, which can be filled into the dispenser using a pump or equivalent device prior to use. Conventional non-aerosol pump spray dispensers, i.e., atomizers, may also be used to apply the formulation to the hair.

Additionally, the formulation, depending on use, may include an oil, a hair conditioning agent, and/or a thickening agent. The cream, lotion, gel, or polish may also include a fragrance, a plant extract, and/or a surfactant. The cream, lotion, gel, or polish may be packaged in a tube, tub, bottle, or other suitable container.

Kits

Some embodiments described herein relate to a kit that can include a cosmetic formulation comprising a compound of Formula (I) or Formula (II), or a combination thereof. In some embodiments, the cosmetic formulation comprises or is a hair treatment formulation, a skin treatment formulation, a nail treatment formulation, or combinations thereof. In further embodiments, the cosmetic formulation is a hair treatment formulation, for example, a hair bleaching formulation, a hair damage repair formulation, a hair styling formulation, or a hair straightening formulation, etc.

In some embodiments, the kit described herein is a hair care kit. In some further embodiments, the kit is a hair bleaching kit, a hair treatment kit, or a hair styling kit. In some embodiments of the kit described herein, the kit may further comprise one or more hair treatment agents. In some embodiments, the one or more hair treatment agents are separated from the formulation containing the compound of Formula (I) or (II) as described herein. For example, the one or more hair treatment agents are in a different container or compartment from the compound of Formula (I) or (II). In some embodiments, different containers may be different bottles, pods, pouches, sachets, or capsules, or combinations thereof. In some embodiments, different compartments may be different compartments of the same bottle, pod, pouch, sachet, capsule, or combinations thereof. For example, in some embodiment, a pod contains a bleaching agent (e.g. a bleaching powder) and a different pod contains the compound of Formula (I) or (II), or the bleaching agent (e.g. a bleaching powder) and the compound of Formula (I) or (II) are contained within the same pod and housed in different compartments. In some embodiments, the structure of the pod is formed from a hydrolyzed poly(vinyl alcohol). In some embodiments, a pod may be multilayered (e.g. comprise a plurality of poly(vinyl alcohol) layers). In some embodiments, the one or more hair treatment agents comprises a bleaching agent, a relaxing agent, a coloring agent, a shampooing agent, or a conditioning agent, or combinations thereof. In some embodiments, the bleaching agent comprises one or more persulfate salts, or one or more peroxides (such as hydrogen peroxide), or a combination thereof. In some embodiments, the persulfate salt comprises or is potassium persulfate, ammonium persulfate, or sodium persulfate, or combinations thereof. In some embodiments, the one or more persulfates has a basic pH of at least about 8, 9 or 10. In some embodiments, the hydrogen peroxide is in a solution having an acid pH of about 3, 4 or 5. In some embodiments, the relaxing agent comprises sodium hydroxide, lithium hydroxide, potassium hydroxide, guanidinium hydroxide, ammonium hydroxide, a sulfite salt, or a thioglycolate salt, or combinations thereof. In some embodiments, the sulfite salt is sodium sulfite or potassium sulfite or a combination thereof.

In one embodiment of the kit described herein, the kit is a hair bleaching kit. The kit may comprise separate containers or compartments for bleach powders (such as one or more persulfate salts described herein), a bleach powder developer (such as hydrogen peroxide solution), and the compound of Formula (I) or (II) as described herein (such as a composition comprising the compound of Formula (I) or (II) and one or more surfactants or other cosmetically acceptable excipients or carrier).

In another embodiment of the kit described herein, the kit is a hair relaxing kit. The kit may comprise separate containers or compartments for one or more relaxing agents (such as sodium hydroxide), and the compound of Formula (I) or (II) as described herein (such as a composition comprising the compound of Formula (I) or (II) and one or more surfactants or other cosmetically acceptable excipients or carrier).

In another embodiment of the kit described herein, the kit is a hair coloring kit. The kit may comprise separate containers or compartments for the coloring agents (e.g., one or more oxidative dyes or direct dyes described herein) and the compound of Formula (I) or (II) as described herein (such as a composition comprising the compound of Formula (I) or (II) and one or more surfactants or other cosmetically acceptable excipients or carrier).

In another embodiment of the kit described herein, the kit is a hair treatment kit. The kit may comprise separate containers or compartments. One container or compartment comprises the active agent (such as a composition comprising the compound of Formula (I) or (II) and one or more surfactants or other cosmetically acceptable excipients or carrier). A second container for mixing the active agent with a cosmetically acceptable carrier (such as purified water).

In another embodiment of the kit described herein, the kit is a hair perming or straightening kit. The kit may comprise separate containers or compartments for one or more reducing agents, an oxidant (such as peroxide or hydrogen peroxide), and the active agent (such as a composition comprising the compound of Formula (I) or (II) and one or more surfactants or other cosmetically acceptable excipients or carrier).

In another embodiment of the kit described herein, the kit is a nail care kit and the kit may further comprise one or more nail treatments or coloring agents. The kit may comprise separate containers. One container comprises the active agent (such as a composition comprising the compound of Formula (I) or (II) in one or more volatile solvents, and optionally also contain or other cosmetically acceptable excipients or carrier). A second container may contain one or more nail coloring agents.

In some embodiments of the kit described herein, an active agent formulation containing a compound of Formula (I) or (II) or a combination thereof (i.e., the active agent) is provided, which is mixed at the time of use with a second formulation, such as a bleaching, coloring, relaxing, or highlighting formulation, or a combination thereof. In these embodiments, the active agent formulation may contain any suitable concentration of active agent in a suitable carrier, typically a diluent, such as described above. The concentration of the active agent is suitable to provide a mixture with the appropriate final volume and final concentration of the active agent. In some embodiments, an active agent formulation can contain a concentration of active agent at, at about, at least, or at least about, 0.1 wt. %, 0.5 wt. %, 0.8 wt. %, 1 wt. %, 1.5 wt. %, 2 wt. %, 2.5 wt. %, 3 wt. %, 3.5 wt. %, 4 wt. %, 4.5 wt. %, 5 wt. %, 5.5 wt. %, 6 wt. %, 6.5 wt. %, 7 wt. %, 7.5 wt. %, 8 wt. %, 8.5 wt. %, 9 wt. %, 9.5 wt. %, 10 wt. %, 11 wt. %, 12 wt. %, 13 wt. %, 14 wt. %, 15 wt. %, 20 wt. %, 25 wt. %, 30 wt. %, 35 wt. %, 40 wt. %, 45 wt. %, 50 wt. %, 60 wt. %, 70 wt. % or 80 wt. %, or a range defined by any two preceding values. For example, an active agent formulation can contain a concentration of active agent ranging from about 1 wt. % to about 50 wt. %, from about 2 wt. % to about 25 wt. %, or from about 5 wt. % to about 10 wt. %.

For bleaching or hair coloring applications, prior to use, a sufficient volume of an active agent formulation (e.g., a liquid active agent formulation) is mixed with a sufficient volume of a highlighting formulation to form a bleaching or hair coloring mixture having the desired concentration of active agent. Typical concentrations of the active agent in the bleaching or hair coloring mixture range from small amounts, such as at least about 0.01 wt. %, about 0.1 wt. %, and up to about 50 wt. %. In some embodiments, the bleaching or hair coloring mixture contains the active agent in a concentration of, of about, of at least, or of at least about, 0.1 wt. %, 0.5 wt. %, 0.8 wt. %, 1 wt. %, 1.5 wt. %, 2 wt. %, 2.5 wt. %, 3 wt. %, 3.5 wt. %, 4 wt. %, 4.5 wt. %, 5 wt.

%, 5.5 wt. %, 6 wt. %, 6.5 wt. %, 7 wt. %, 7.5 wt. %, 8 wt. %, 8.5 wt. %, 9 wt. %, 9.5 wt. %, 10 wt. %, 11 wt. %, 12 wt. %, 13 wt. %, 14 wt. %, 15 wt. %, 20 wt. %, 30 wt. %, 40 wt. %, 50 wt. %, 60 wt. % or 70 wt. %, or a range defined by any two preceding values. Preferably the bleaching or hair coloring mixture contains the active agent in a concentration ranging from about 0.1 wt. % to about 50 wt. %, from about 0.5 wt. % to about 25 wt. %, from about 1 wt. % to about 20 wt. %, from about 2 wt. % to about 15 wt. %, or from about 5 wt. % to about 10 wt. %.

In particular embodiments of the hair treatment kit, the kit typically contains a first formulation for coloring, bleaching hair, straightening or perming hair. In some such embodiments, the first formulation in the kit can be a coloring treatment. In other such embodiments, the first formulation in the kit is a bleaching treatment. The first formulation may be formulated as two or more components which may be mixed together before application to the hair. For example, the first formulation may be in the form of two components, such as a dye precursor and an oxidant, a bleach powder and a developer, or a reducing agent and an oxidant (such as a peroxide). In some embodiments, the hair coloring or bleaching formulation comprises a reducing agent. Suitable reducing agents include, but are not limited to, thioglycolic acid, thiolactic acid, dihydrolipoate, thioglycerol, mercaptopropionic acid, sodium bisulfate, ammonium bisulfide, zinc formaldehyde sulfoxylate, sodium formaldehyde sulfoxylate, sodium metabisulfite, potassium borohydride, pegylated thiols and hydroquinone. The components of the first formulation may differ depending on the hair coloring treatment desired (such as for semi-permanent, demi-permanent, or permanent hair color), the texture of the hair, the sensitivity of the user's skin, and such the like. Hair coloring formulations for different hair coloring treatment, hair texture, and hair sensitivity are known to those of skill in the art. The kit also includes a second formulation containing an effective amount of the compound of Formula (I) or (II) or a combination thereof (i.e., the active agent formulation). Suitable formulations containing the active agents are discussed above. The second formulation may be in any suitable form. Suitable forms include, but are not limited to, low to moderate viscosity liquids, pastes, lotions, milks, mousses, sprays, gels, creams, shampoos, conditioners, and the like. In further embodiments, the active agent formulation comprises, consisting of, or consisting essentially of the compound of Formula (I) or (II), and one or more surfactants. In one embodiment, the active agent formulation is in the form of a paste comprising, consisting of, or consisting essentially of about 80 wt. % of the compound of Formula (I) or (II), and about 20 wt. % of behentrimonium chloride. The second formulation will be present in a suitable container or compartment, which depends on the form of the formulation. In some embodiments, the active agent formulation is provided as two or more separate ingredients. For example, the active agent may be provided in a sealed package and the excipient provided in a vial, another container, or another compartment. A suitable mixing container for the active agent and the excipient may be provided. In some embodiments, the active agent formulation (or second formulation) is mixed with the first formulation (e.g., hair bleaching, coloring, straightening or relaxing treatment), and the mixture is applied to the hair.

The kit may further include a developer bottle, gloves, shampoo, conditioner, and/or an odor eliminator. Instructions for use of the kit are also typically provided. Typically, the kit contains more than one container (or more than one compartment in a given container) to ensure that the lightening agent (e.g., peroxides) or the coloring agent is stored separately from the active agent.

Other Materials in the Cosmetic Formulation or Kit

The kit for hair treatment may optionally contains shampoos and/or conditioners. The kit may further contain an odor eliminator. The odor eliminator can be incorporated into the first or second formulation, or a mixture thereof. Alternately, the odor eliminator is present in a suitable container or compartment for use before or after washing the second formulation from the hair. Some suitable odor eliminators are known to those of ordinary skill in the art.

In some embodiments of the cosmetic formulation or kit described herein, the cosmetic formulation or kit may further comprise small or trace amount of maleic acid or a maleate salt (i.e., maleic acid is anionic form with a cationic counterion). In some embodiments, the maleic acid or salt thereof in the cosmetic formulation or kit comprises is about, or less than about 0.5 wt. %, 0.4 wt. %, 0.3 wt. %, 0.2 wt. %, 0.1 wt. %, 0.09 wt. %, 0.08 wt. %, 0.07 wt. %, 0.06 wt. %, 0.05 wt. %, 0.04 wt. %, 0.03 wt. %, 0.02 wt. %, or 0.01 wt. %, or in a range defined by any two of the preceding values.

Methods of Use

Some embodiments provided herein relate to a method of treating hair, skin and/or nails that can include administering to a subject a cosmetic formulation that can include an effective amount of one or more diester compounds described herein, for example a compound of Formula (I) or Formula (II). Some embodiments provided herein relate to a method of treating hair that can include administering and/or applying to hair a cosmetic formulation that can include an effective amount of one or more diester compounds of Formula (I) or Formula (II) or a combination thereof, as described herein. Some embodiments provided herein relate to a method of treating skin that can include administering and/or applying to skin a cosmetic formulation that can include an effective amount of one or more diester compounds of Formula (I) or Formula (II) or a combination thereof, as described herein. Some embodiments provided herein relate to a method of treating nails that can include administering and/or applying to nails a cosmetic formulation that can include an effective amount of one or more diester compounds of Formula (I) or Formula (II) or a combination thereof, as described herein. In some embodiments, administering and/or applying the cosmetic formulation may be performed by spraying, rubbing, pouring and/or brushing the cosmetic formulation onto the hair, skin and/or nails, and/or dipping the hair, skin and/or nails into the cosmetic formulation. In some embodiments, the cosmetic formulation (e.g. the hair, skin and/or nail treatment formulation) is formed by mixing the one or more diester compounds described herein (e.g., a compound of Formula (I) or Formula (II)) with a cosmetically acceptable carrier and/or hair treatment agent.

Some embodiments of the method relate to a method of bleaching hair, comprising applying a cosmetic formulation to the hair, wherein the cosmetic formulation comprises a bleaching formulation, and a compound of Formula (I) or (II), or a combination thereof as described herein, wherein the amount of compound of Formula (I) or (II) in the cosmetic formulation is at least about 1% by weight, and wherein in the cosmetic formulation has a basic pH of greater than about 9. In further embodiments, the cosmetic formulation comprises about 2 wt. % to about 20 wt. %, or about 3 wt. % to about 15 wt. %, or about 5 wt. % to about 10 wt. % of the compound of Formula (I) of (II). In some embodiments, the method of bleaching hair does not comprise applying a coloring agent and/or a dye (e.g. an oxidative dye and/or a direct dye) to the hair. In some embodiments, the method of bleaching hair further comprises applying a coloring agent and/or a dye (e.g. an oxidative dye and/or a direct dye) to the hair.

In some embodiments, the method further comprises combining the bleaching formulation and the compound of Formula (I) or (II) to form the cosmetic formulation. In some embodiments, the cosmetic formulation is formed within about 1 to 3 hours before being applied to the hair. In other embodiments, the cosmetic formulation is formed within about 30 minutes or less before being applied to the hair. In some embodiments, the cosmetic formulation is formed on hair by applying the formulation and the compound of Formula (I) or (II) on the hair, either sequentially or simultaneously. As such, the step of applying the cosmetic formulation to the hair comprises applying the bleaching formulation and the compound of Formula (I) or (II) on the hair to form the cosmetic formulation. In some embodiments, the bleaching formulation is applied to the hair prior to applying the compound of Formula (I) or (II) to the hair. In some embodiments, the bleaching formulation is applied to the hair subsequent to applying the compound of Formula (I) or (II) to the hair. In further embodiments, the bleaching formulation may be prepared by mixing a bleach powder comprises one or more persulfate salts with a developer. In some such embodiments, the persulfate salt comprises or is potassium persulfate, ammonium persulfate, or sodium persulfate, or combinations thereof. In some such embodiments, the developer comprises or is hydrogen peroxide.

In some embodiments, the compound of Formula (I) or (II) is in a separate composition (i.e., active agent formulation). The active agent formulation may comprise at least or up to 5%, 10%, 15% or 20% of one or more surfactants (for example, a cationic surfactant such as behentrimonium chloride and/or behentrimonium methosulfate) prior to combining with the bleaching formulation. As such, the cosmetic formulation is formed by combining the beaching formulation with the composition comprising the compound of Formula (I) or (II).

In some embodiments, the method further comprises rinsing the hair after applying the cosmetic formulation. In further embodiments, the method may further comprise applying a hair conditioning formulation (e.g., cream, gel, paste, spray, etc.) to the hair after the rinsing step. In some such embodiments, the hair conditioning formulation may comprise the compound of Formula (I) or (II) described herein, for example, the hair treatment formulation described herein used in the method of treating hair to reduce or prevent hair breakage. In some further embodiments, the breakage of the hair is decreased by at least 5%, 10%, 15% or 20%, compared to hair bleached with the bleaching formulation in the absence of the compound of Formula (I) or (II). For example, hair breakage may be decreased by at least 10%, 15%, 20%, 25%, 30%, 35%, 40%, 45%, 50% compared to untreated hair, when the hair styling formulation is used at least 2-3 times/week for at least 2 weeks, 3 weeks, 1, 2, 3, 4, 5 or 6 months.

Some additional embodiments relate to a method of treating hair to reduce or prevent hair breakage, comprising: applying a hair treatment formulation to damaged hair, wherein the hair treatment formulation comprises a compound of Formula (I) or (II) or a combination thereof, and a cosmetically acceptable carrier, wherein breakage of the hair is decreased by at least 5% compared to untreated hair, or hair treated with a repair formulation that does not contain the active agent described herein (i.e., the diester compound). In some embodiments, the amount of compound of Formula (I) or (II) in the hair treatment formulation is at least about 1%, 2%, 3%, 4%, 5%, 6%, 7%, 8%, 9%, 10%, 15% or 20% by weight, or a range defined by any two of the preceding values. For example, the amount of compound of Formula (I) or (II) in the hair treatment formulation is at least about 5% to about 10% when the hair is coarse or heavily damaged (e.g., have been previously subject to repeated coloring, bleaching, perming, relaxing, straightening, or heat styling, etc.). In some embodiments, the damaged hair is caused by bleaching, relaxing, coloring, perming, straightening, or heat styling, or combination thereof. In some embodiments, the hair treatment formulation is applied to the hair 1, 2, 3, 4, 5, 6, 7, 8, 9 or 10 times a week, to achieve the decreased hair breakage and improved hair quality over time. For example, hair breakage may be decreased by at least 10%, 15%, 20%, 25%, 30%, 35%, 40%, 45%, 50% compared to untreated hair, when the hair styling formulation is used at least 2-3 times/week for at least 2 weeks, 3 weeks, 1, 2, 3, 4, 5 or 6 months.

In some embodiments, the hair treatment formulation is formed by mixing the compound of Formula (I) or (II) in a cosmetically acceptable carrier. In some such embodiments, the cosmetically acceptable carrier comprises or is water, purified water, or deionized water. In some embodiments, the compound of Formula (I) or (II) is in a separate composition comprising at least or at most about 5% to 20% of one or more surfactants (for example, a cationic surfactant such as behentrimonium chloride and/or behentrimonium methosulfate) prior to mixing with the cosmetically acceptable carrier. As such, the hair treatment formulation is formed by combining the composition comprising the compound of Formula (I) or (II) with the cosmetically acceptable carrier (e.g., purified water). In some embodiments, the method further comprises rinsing the hair after applying the hair treatment formulation. In other embodiments, the method does not require rinsing the hair after applying the hair treatment formulation. In further embodiments, applying the hair treatment formulation comprises spraying the hair treatment formulation onto the damage hair.

Some additional embodiments relate to a method of styling hair, comprising: applying a hair styling formulation to the hair, wherein the hair styling formulation comprises a compound of Formula (I) or (II) or a combination thereof as described herein; and treating hair with a heated hair styling tool. In some embodiments, the method further comprises blow drying the hair prior to treating the hair with the heated styling tool. In further embodiments, the amount of compound of Formula (I) or (II) in the hair styling formulation is at least about 0.5%, 1%, 2%, 3%, 4%, 5%, 6%, 7%, 8%, 9%, 10%, 15% or 20% by weight. For example, the amount of compound of Formula (I) or (II) in the hair styling formulation is at least about 5% to about 10% when the hair is coarse or heavily damaged (e.g., have been previously subject to repeated coloring, bleaching, perming, relaxing, straightening, or heat styling, etc.). In some embodiments, the method further comprises rinsing the hair after applying the hair styling formulation. In other embodiments, the method does not require rinsing the hair after applying the hair styling formulation. In some embodiments, the method straightens the hair. In some embodiments, the hair styling formulation is applied to the hair 1, 2, 3, 4, 5, 6, 7, 8, 9 or 10 times a week, to achieve the decreased hair breakage and improved hair quality over time. For example, hair breakage may be decreased by at least 10%, 15%, 20%, 25%, 30%, 35%, 40%, 45%, 50% compared to untreated hair, when the hair styling formulation is used at least 2-3 times/week for at least 2 weeks, 3 weeks, 1, 2, 3, 4, 5 or 6 months.

Some additional embodiments relate to a method of perming hair, comprising: applying a reducing agent to the hair; and applying a perming formulation to the hair, wherein the perming formulation comprises a compound of Formula (I) or (II) or a combination thereof as described herein. In further embodiments, the amount of compound of Formula (I) or (II) in the perming formulation is at least about 0.5%, 1%, 2%, 3%, 4%, 5%, 6%, 7%, 8%, 9%, 10%, 15% or 20% by weight. For example, the amount of compound of Formula (I) or (II) in the perming formulation is at least about 5% to about 10% when the hair is coarse or heavily damaged (e.g., have been previously subject to repeated coloring, bleaching, perming, relaxing, straightening, or heat styling, etc.). In some embodiments, the method further comprises rinsing the hair after applying the reducing agent. In some embodiments, the method further comprises rinsing the hair after applying the perming formulation. In further embodiments, the method may also comprise styling hair with a heated hair styling tool. In some embodiments, the reducing agent comprises or is thioglycolic acid, thiolactic acid, dihydrolipoate, thioglycerol, mercaptopropionic acid, sodium bisulfite, ammonium bisulfide, zinc formaldehyde sulfoxylate, sodium formaldehyde sulfoxylate, sodium metabisulfite, potassium borohydride, pegylated thiols, or hydroquinone, or combinations thereof. In some embodiments, the reducing agent is applied to the hair prior to the perming formulation being applied to the hair. In some such embodiments, the perming formulation is applied to the hair at, at about, at most, at most about, at least, or at least about, 30 seconds, 1 minute, 5 minutes, 10 minutes, 15 minutes, 30 minutes, or 1 hour after the application of the reducing agent. In some embodiments, the reducing agent is applied to the hair concurrently with the styling formulation. In some embodiments, the method further comprises washing, rinsing, or drying, or a combination thereof, of the hair after the application of the reducing agent and before the application of the perming formulation. In further embodiments, the perming formulation further comprises an oxidant (e.g., a peroxide). In some embodiments, the method may achieve decreased hair breakage and improved hair quality compared to a perming method when the perming formulation with the active agent (e.g., the compound of Formula (I) or (II)). For example, hair breakage may be decreased by at least 10%, 15%, 20%, 25%, 30%, 35%, 40%, 45%, 50% compared to using a perming formulation without the active agent.

Some additional embodiments relate to a method of treating nail, comprising: applying a nail treatment formulation to one or more nails, wherein the nail treatment formulation comprises a compound of Formula (I) or (II) or a combination thereof as described herein, and one or more volatile solvents. In some embodiments, the amount of the compound of Formula (I) or (II) in the nail treatment formulation is at least 0.1%, 0.2%, 0.3%, 0.4%, 0.5%, 1%, 2%, 3%, 4%, 5%, 6%, 7%, 8%, 9%, 10%, 15%, 20%, 25%, 30%, 35%, 40%, 45%, 50%, 55%, 60% or 70% by weight, or in a range defined by any two of the preceding values. In some embodiments, the one or more volatile solvents comprise or is ethyl acetate, or acetone, or a combination thereof. In some embodiments, the method further comprises washing, rinsing, or drying, or a combination thereof, of one or more nails prior to the application of the nail treatment formulation. In some embodiments, the nail treatment formulation is applied to one or more nails as a nail base coat or a nail primer before applying a nail coloring agent. For example, the nail treatment formulation is applied to one or more nails for at least about 1 minute, 5 minutes, 10 minutes, or 1 hour prior to the application of the nail coloring agent. In other embodiments, the nail treatment formulation is applied after the nail coloring. In still other embodiments, the nail treatment formulation may be combined with one or more nail coloring agents or a nail coloring formulation and are applied to the nail simultaneously.

Some additional embodiments relate to a method of applying a skin treatment or anti-aging formulation to the skin. In some embodiments, the skin treatment or anti-aging formulation comprises a compound of Formula (I) or (II) or a combination thereof as described herein. In some embodiments, the amount of the compound of Formula (I) or (II) in the skin treatment or anti-aging formulation is at least 0.1%, 0.5%, 1%, 5%, 6%, 7%, 8%, 9%, or 10%, or in a range defined by any two of the preceding values. Alternatively, the compound of Formula (I) or (II) is in a separate active agent formulation and can be applied to the skin prior to or after the skin treatment or anti-aging formulation. In some embodiments, the skin is washed, rinsed, and/or dried prior to the application of the active agent formulation.

Methods of Using Hair Treatment Kits

In some embodiments, the active agent formulation is in a kit and the kit may further comprise additional hair treatment agent(s) or formulation(s), such as a hair bleaching agent or formulation, a hair coloring agent or formulation, a hair relaxing agent or formulation, a hair perming agent or formulation, or a hair straightening agent or formulation. In some embodiments, the active agent formulation containing the diester compound(s) is applied to the hair after the application of the hair treatment agent(s). In some embodiments, the active agent formulation is applied to the hair at, at about, at most, at most about, at least, or at least about, 30 seconds, 1 minute, 5 minutes, 10 minutes, 15 minutes, 30 minutes, 1 hours, 2 hours, 3 hours, 4 hours, 6 hours, 12 hours, 18 hours, 24 hours or 30 hours after the application of the hair treatment agent(s). In some embodiments, the active agent formulation is applied to the hair at least 24 hours after the application of the hair treatment agent(s). In other embodiments, the active agent formulation is applied to the hair within about 1 to 3 hours, within about 30 minutes, or within about 1 minute after the application of the hair treatment agent(s). In some embodiments, the hair is washed, rinsed, and/or dried to substantially remove any remaining hair treatment agent prior to the application of the active agent formulation.

In some other embodiments, the active agent formulation is applied to the hair prior to the application of the hair treatment agent(s). In some embodiments, the cosmetic formulation is applied to the hair at, at about, at least, or at least about, 30 seconds, 1 minute, 5 minutes, 10 minutes, 15 minutes, 30 minutes, 1 hours, 2 hours, 3 hours, 4 hours, 6 hours, 12 hours, 18 hours, 24 hours or 30 hours prior the application of the hair treatment agent(s). In some embodiments, the active agent formulation is applied to the hair at least 24 hours prior to the application of the hair treatment agent(s). In other embodiments, the active agent formulation is applied to the hair within about 1 to 3 hours, within about 30 minutes, or within about 1 minute prior to the application of the hair treatment agent(s). In some embodiments, the hair is washed, rinsed, and/or dried to substantially remove any remaining cosmetic formulation prior to the application of the hair treatment agent(s).

In some embodiments, the active agent formulation and the hair treatment agent(s) are applied to the hair simultaneously. In some embodiments, the active agent formulation and the hair treatment agent(s) are premixed as a hair application mixture prior to being applied to the hair. In some embodiments, the hair application mixture is premixed at, at about, at most, at most about, at least, or at least about, 30 seconds, 1 minute, 5 minutes, 10 minutes, 15 minutes, 30 minutes, 1 hours, 2 hours, 3 hours, 4 hours, 6 hours, 12 hours, 18 hours, 24 hours or 30 hours before being applied to the hair. In some embodiments, the hair application mixture is premixed at least 24 hours prior to being applied to the hair. In other embodiments, the hair application mixture is premixed within about 1 to 3 hours, within about 30 minutes, or within about 1 minute before being applied to hair. In some embodiments, the method further comprises rinsing the hair after the application of the hair application mixture.

Hair breakage is a significant problem encountered during bleaching, relaxing, perming, coloring and other treatments of hair. Applying the cosmetic formulation described herein to hair may achieve a reduced breakage of the hair relative to hair treated with a hair treatment agent (e.g. a bleaching formulation) and/or cosmetic formulation in the absence of the compound of Formula (I) or Formula (II). In some embodiments, breakage of the hair is decreased by, by about, by at least, or by at least about, 0.5%, 1%, 2%, 3%, 4%, 5%, 6%, 8%, 10%, 12%, 15%, 20%, 25%, 30%, 35%, 40%, 45% or 50%, or a range defined by any two of the preceding values. In some embodiments, the cosmetic formulation is applied to untreated hair. In some embodiments, the untreated hair is virgin hair, or is bleached hair and/or colored hair, or is damaged hair has been treated with other hair repair agent that does not contain the diester compound described herein. In some embodiments, the hair breakage is reduced by at least 10%, 15%, 20%, 25%, 30%, 35%, 40%, 45%, or 50%, compared to untreated hair, when the cosmetic formulation containing compound of Formula (I) or Formula (II) have been used at least 1-3 times/week for at least 2 weeks, 3 week, 1, 2, 3, 4, 5 or 6 months.

In any embodiments of the method described herein, the cosmetic formulation or the active agent formulation comprises a compound of Formula (I), where each of $R^1$ and $R^2$ is independently selected from the group consisting of an optionally substituted $C_8$ alkyl, and each of $R^A$ and $R^B$ is hydrogen. In further embodiments, the compound of Formula (I) is dioctyl maleate or bis(2-ethylhexyl) maleate, or a combination thereof.

EXAMPLES

Additional embodiments are disclosed in further detail in the following examples, which are not in any way intended to limit the scope of the claims.

Example 1

Cosmetic formulations were prepared and tested on hair to evaluate the effect the diester compound disclosed herein on bleached hair.

Formula A (control) includes: 16 g of bleach powder (Clairol Professional® BW2 Dedusted Extra Strength), and 16 g of developer (Clairol Professional® Pure White crème developer 40 volume). Formula B includes: 15 g of bleach powder (Clairol Professional® BW2 Dedusted Extra Strength), 15 g of developer (Clairol Professional® Pure White crème developer 40 volume), and 1.9 g active agent containing paste which consists of 80 wt. % bis(2-ethylhexyl) maleate (Sigma-Aldrich) and 20 wt. % behentrimonium chloride. Formula C includes: 15 g of bleach powder (Clairol Professional® BW2 Dedusted Extra Strength), 15 g of developer (Clairol Professional® Pure White crème developer 40 volume), and 0.5 g active agent containing paste which consists of 80 wt. % bis(2-ethylhexyl) maleate (Sigma-Aldrich) and 20 wt. % behentrimonium chloride. Medium, medium dark and dark color hair swatches each of 5 cm*1.3 cm Indian hair (Pivot Point) were utilized. Additionally, virgin medium dark swatches of Caucasian hair were used (~25 cm*1.3 cm). All components of Formulae A, B or C were combined in a mixing bowl, stirred until even mixed, and then brushed onto each of the hair swatches. Each of the hair swatches coated with Formulae A, B and C were closed into aluminum foil and left for 2 hours. The swatches were then rinsed, washed with shampoo, and then air dried.

Results are shown in FIG. 1, which show hair swatches treated with Formulae A (left), B (middle) and C (right). A noticeable difference in hair quality was observed in the hair swatches treated with the three Formulae. The swatches treated with Formula B and Formula C were of much better condition relative to the swatches treated with Formula A, wherein the Formula B and C swatches showed less breakage, better feel and easier combing and styling. The lighting effect of both formulas was similar. Formula B had slightly improved feel and easier combing than Formula C. When Formula B was touched by hand, it was noticed to not have the typical burning sensation one experiences with touching a bleach formulation.

Example 2

A cosmetic formulation was prepared to test the effect the diester compound disclosed herein on bleach damaged hair and African American hair.

Formula D was prepared by mixing 50 g distilled water, 1.6 g bis(2-ethylhexyl) maleate (Sigma-Aldrich) and 0.4 g behentrimonium chloride. The mixed solution was applied to bleached damaged hair for 10 minutes, 30 minutes, 1 hour and 16 hours before shampooing and drying the bleached damaged hair. A bleach damaged hair sample that was not treated with Formula D was used as a control. The mixed solution was also applied to African American hair for 16 hours, and an African American hair sample that was not treated with Formula D was used as a control.

Figure 2:
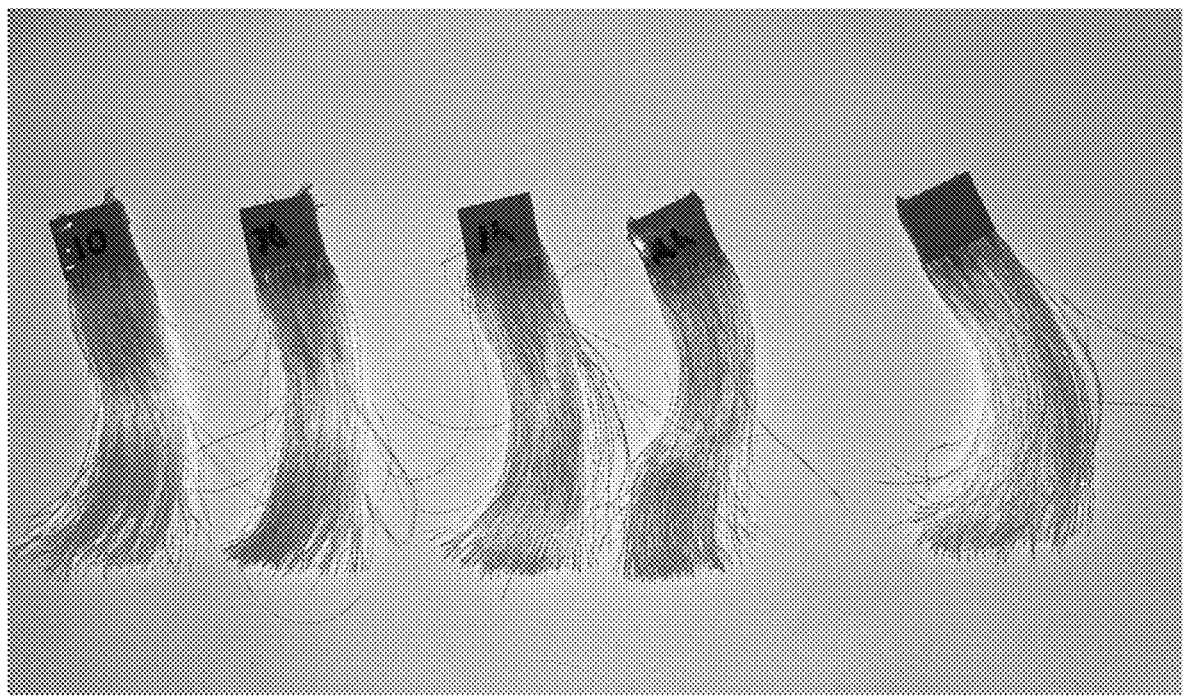
FIG. 2 is a photograph of bleach damaged hair swatches treated with cosmetic Formula D for 10 minutes, 30 minutes, 1 hour, 16 hours, or untreated (from left to right respectively).
Figure 3:
FIG. 3 is a photograph of an untreated bleach damaged hair swatch (left) and a bleach damaged hair swatch treated with cosmetic Formulae D (right).
Figure 4:
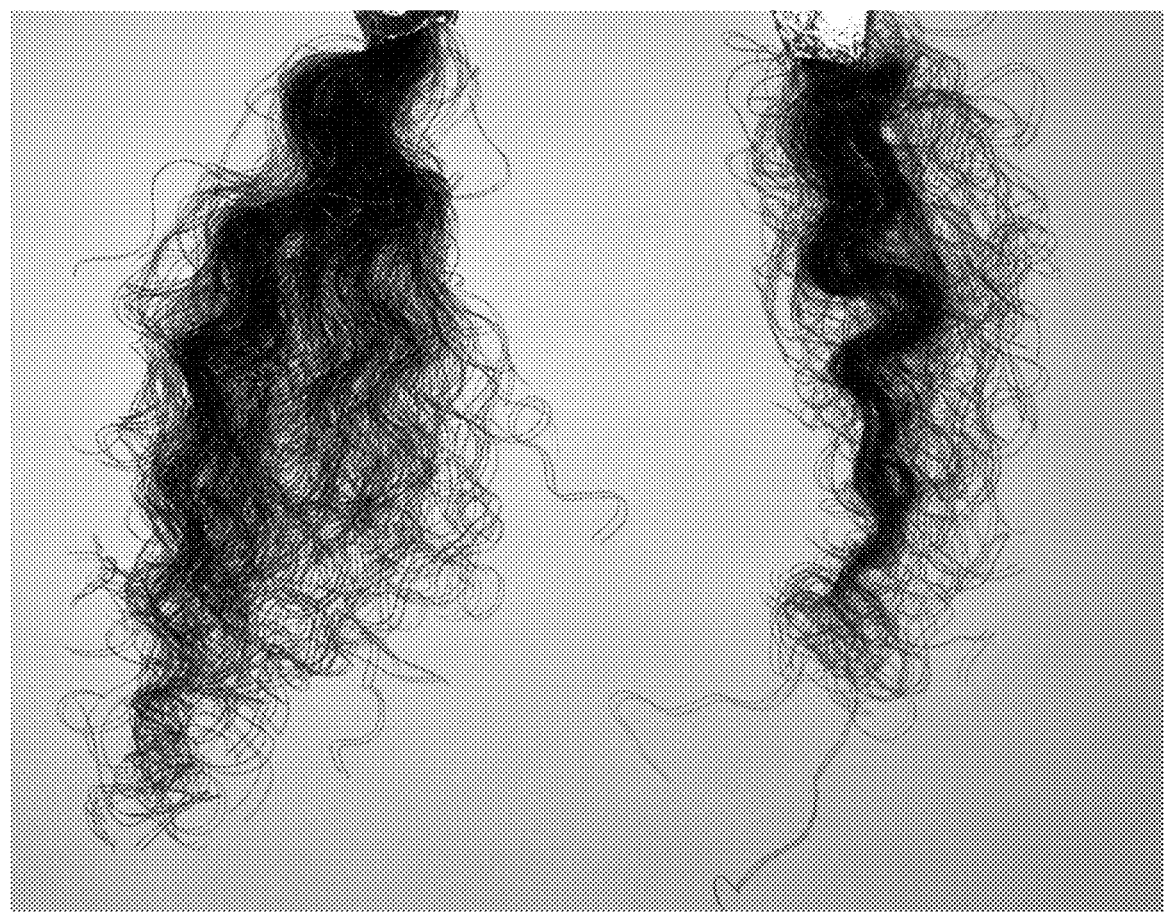
FIG. 4 is a photograph of an untreated African American hair swatch (left) and an African American hair swatch treated with cosmetic Formula D (right).

Results are shown in FIG. 2, which show bleached damaged hair treated with Formula D for 10 minutes, 30 minutes, 1 hour and 16 hours, and control, respectively from left to right. FIG. 3 also shows results for untreated bleach damaged hair (left) and bleach damaged hair treated with Formula D for 16 hours (right). FIG. 4 shows results for untreated African American hair (left) and African American hair treated with Formula D for 16 hours (right). As seen in FIGS. 2-4, hair (i.e. bleached damaged hair and African American hair) treated with Formula D showed increased shine, increased softness, increased combing ability and decreased appearance of frizz relative to the controls.

Example 3

Cosmetic formulations were prepared to evaluate the effect of the diester compound disclosed herein on color treated hair.

Formula E includes: 10 g of Igora Royal color (1-0 color) and 10 g Igora Royal oil developer (20 volume). Formula F includes: 10.5 g of Igora Royal color (1-0 color) and 10.5 g Igora Royal oil developer (20 volume) and 0.55 g active agent containing paste which consists of 80 wt. % bis(2-ethylhexyl) maleate (Sigma-Aldrich) and 20 wt. % behentrimonium chloride. All components of Formulae E or F were combined in a mixing bowl, stirred until even mixed, and then brushed onto the hair swatches. Medium blonde, grey color hair swatches each of 5 cm*1.3 cm Indian hair (Pivot Point) were utilized. Additionally, virgin blonde swatches of Caucasian hair were used (~20 cm*1.3 cm). Each of the hair swatches coated with Formulae E or F were closed into aluminum foil and left for 45 minutes. The swatches were then rinsed, washed with shampoo, and then air dried.

Figure 5:
FIG. 5 is a photograph of blonde hair swatches treated with cosmetic Formula E or F (from left to right respectively).

Results are shown in FIG. 5, with Formula E treated hair (left) and Formula F treated hair (right). The swatches treated with Formula F were much softer, had better condition and significantly less frizz than the swatches treated with Formula E.

Example 4

Cosmetic formulations were prepared to evaluate the effect of the diester compound disclosed herein on chemically relaxed hair.

Formula G includes: Mizani Butter Blend Relaxer Medium. Formula H includes: Mizani Butter Blend Relaxer Medium (15.7 g) and bis(2-ethylhexyl) maleate (1.6 g). Formulae G and H were both applied to African American hair swatches with the back of a comb and were finger pulled to straighten over 18 minutes. Both were then thoroughly rinsed and shampooed.

Figure 6:
FIG. 6 is a photograph of hair swatches treated and relaxed with cosmetic Formula G or H (from left to right respectively).

Results are shown in FIG. 6, with Formula G treated hair (left) and Formula H treated hair (right). Both swatches relaxed significantly to an equal degree, but the swatch of Formula H had improved ease of combing, a softer feel, and far less damaged ends.

Example 5

Cosmetic formulations were prepared to evaluate the effect of the diester compound disclosed herein on the perming of hair.

Formula I includes: Zotos Quantum Firm Options Perm used as directed. Formula J includes: Zotos Quantum Firm Options Perm, first step as directed and neutralized lotion (19 g) had 0.94 g active agent containing paste which consists of 80 wt. % bis(2-ethylhexyl) maleate (Sigma-Aldrich) and 20 wt. % behentrimonium chloride added. Formulae I and J were both applied to Caucasian hair swatches (~25 cm long) that were wrapped on peach color size perm rods, 20 minutes for the perming lotion, 5 minutes rinse, 5 minutes neutralizing solution, one more minute of neutralizing solution while removing rods and 3 minutes of rinsing before air drying. Both hair swatches were then shampooed 48 hours later.

Both swatches retained curl, but the swatch of Formula J had improved ease of combing, a softer feel, and less damaged ends.

Example 6

Cosmetic formulations were prepared to evaluate the effect of the diester compound disclosed herein on nails.

Two nail treatment formulations were made both containing bis(2-ethylhexyl) maleate in ethyl acetate, wherein the first nail treatment formulation contains 7 wt. % bis(2-ethylhexyl) maleate and the second nail treatment formulation contains 20 wt. % bis(2-ethylhexyl) maleate. These two nail treatment formulations containing were applied to nails and compared against the ethyl acetate control formulation. The nails were treated for 10 min by applying the formulation by nail polish brush, after which any excess was rubbed away.

The nails treated with the first and second nail treatment formulations demonstrate better condition relative to the nails treated with the control formulation. Nails treated with the first and second nail treatment formulations demonstrated an increase in shine, softness and overall appearance. The appearance effect could best be compared to a fresh buffing. The effects were shown to last greater than a week and are more pronounced on damaged nails. Multiple treatments were shown to increase improvement.

Example 7

Cosmetic formulations were prepared to evaluate the effect of the diester compound disclosed herein on bleached hair in comparison to a commercial hair repair treatment.

Formula K includes: 17 g of bleach powder (Clairol Professional® BW2 Dedusted Extra Strength), 17 g of developer (Clairol Professional® Pure White crème developer 40 volume), and 2.4 g active agent containing paste which consists of 80 wt. % bis(2-ethylhexyl) maleate (Sigma-Aldrich) and 20 wt. % behentrimonium chloride.

Formula L includes: 19 g of bleach powder (Clairol Professional® BW2 Dedusted Extra Strength), 19 g of developer (Clairol Professional® Pure White crème developer 40 volume), and 2.5 g Olaplex® Bond Multiplier Number One solution.

Medium, medium dark and dark color hair swatches each of 5 cm*1.3 cm Indian hair (Pivot Point) were utilized. All components of Formulae K or L were combined in a mixing bowl, stirred until even mixed, and then brushed onto each of the hair swatches. Each of the hair swatches coated with Formulae K or L were closed into aluminum foil and left for 45 minutes. The swatches were then rinsed, washed with shampoo, and then air dried.

A noticeable difference in hair quality was observed in the hair swatches treated with the two Formulae. The swatches treated with Formula K felt better, looked better and had a slightly better combability than Formula L. In addition, Formula K lightened the hair to a greater extent when compared to the lightening effect of Formula L.

What is claimed is:

1. A method of treating hair to reduced or prevent breakage, comprising:
   mixing a cosmetic formulation with a cosmetically acceptable carrier to form a hair treatment formulation;
      wherein the cosmetic formulation comprises bis(2-ethylhexyl) maleate and one or more surfactants, wherein the amount of bis(2-ethylhexyl) maleate in the cosmetic formulation is at least about 70% by weight, and wherein the amount of the one or more surfactants in the cosmetic formulation is about 0.5-10% by weight;
      wherein the cosmetically acceptable carrier comprises water; and
      wherein the hair treatment formulation comprises at least about 50 wt. % of water; and
   applying the hair treatment formulation to damaged hair, wherein breakage of the hair is decreased by at least 5% compared to untreated hair.

2. The method of claim 1, wherein the damaged hair is caused by bleaching, relaxing, coloring, perming, or heat styling, or combinations thereof.

3. The method of claim 1, wherein the hair treatment formulation further comprises a coloring agent, a shampooing agent, or a conditioning agent, or combinations thereof.

4. The method of claim 1, wherein the water is purified water.

5. The method of claim 1, wherein the one or more surfactants in the cosmetic formulation comprises a cationic surfactant.

6. The method of claim 1, wherein the cosmetic formulation further comprises a cosmetically acceptable diluent.

7. The method of claim 6, wherein the cosmetically acceptable diluent in the cosmetic formulation comprises an alcohol.

8. The method of claim 7, wherein the amount of the alcohol in the cosmetic formulation is about 1-10% by weight.

9. The method of claim 1, further comprising rinsing the hair treatment formulation applied to the hair.

10. The method of claim 1, wherein the amount of bis(2-ethylhexyl) maleate in the cosmetic formulation is at least about 80% by weight.

11. The method of claim 1, wherein the amount of bis(2-ethylhexyl) maleate in the cosmetic formulation is about 70-95% by weight.

12. The method of claim 1, wherein the amount of the one or more surfactants in the cosmetic formulation is about 1-5% by weight.

13. The method of claim 1, wherein the hair treatment formulation further comprises one or more cosmetically acceptable excipients selected from the group consisting of a vitamin, a natural extract, a preservative, an antioxidant, a chelating agent, a protein, an amino acid, a humectant, a fragrance, an emollient, a penetrant, a thickener, a viscosity modifier, a hair fixative, a film former, an emulsifier, an opacifying agent, a propellant, a carrier, a salt, a buffer, an anti-static agent, an anti-frizz agent, an anti-dandruff agent, and a colorant, and combinations thereof.

14. The method of claim 1, wherein the one or more surfactants is selected from the group consisting of 3-aminopropane sulfonic acid, almond amide, almond amidopropyl betaine, almond amidopropylamine oxide, aluminum hydrogenated tallow glutamate, aluminum lanolate, aminoethyl sulfate, aminopropyl lauryl glutamine, ammonium C12-15 alkyl sulfate, ammonium C12-15 pareth sulfate, ammonium C12-16 alkyl sulfate, ammonium C9-10 perfluoroalkylsulfonate, ammonium capryleth sulfate, ammonium capryleth-3 sulfate, ammonium monoglyceride sulfate, ammonium sulfate, ammonium isothionate, ammonium cocoyl sarcosinate, ammonium cumene sulfonate, ammonium dimethicone copolyol sulfate, ammonium dodecylbenzenesulfonate, ammonium isostearate, ammonium laureth sulfate, ammonium laureth-12 sulfate, ammonium laureth-5 sulfate, ammonium laureth-6 carboxylate, ammonium laureth-7 sulfate, ammonium laureth-8 carboxylate, ammonium laureth-9 sulfate, ammonium lauroyl sarcosinate, ammonium lauryl sulfate, ammonium lauryl sulfosuccinate, ammonium myreth sulfate, ammonium myristyl sulfate, ammonium nonoxynol-30 sulfate, ammonium nonoxynol-4 sulfate, ammonium oleate, ammonium palm kernel sulfate, ammonium polyacrylate, ammonium stearate, ammonium tallate, ammonium xylene sulfonate, ammonium xylene sulfonate, amp-isostearoyl gelatin/keratin amino acids/lysine hydroxypropyltrimonium chloride, amp-isostearoyl hydrolyzed collagen, apricot kernel oil PEG-6 esters, apricot amide, apricot amidopropyl betaine, arachideth-20, avocadamide, avocadamidopropyl betaine, babassuamide, babassuamidopropyl betaine, babassuamidopropylamine oxide, behenalkonium chloride, behenamide, behenamide, behenamidopropyl betaine, behenamine oxide, sodium laureth sulfate, sodium lauryl sulfate, a polyoxyether of lauryl alcohol, ceteareth-20, and combinations thereof.

15. The method of claim 1, wherein the one or more surfactants in the cosmetic formulation comprises an anionic surfactant.

16. The method of claim 15, wherein the anionic surfactant is selected from the group consisting of sodium dodecylbenzene sulfonate, potassium dodecylbenzene sulfonate, ammonium dodecylbenzene sulfonate, sodium dodecylbenzene sulfonate, sodium bis-(2-ethylthioxyl)-sulfosuccinate, sodium lauryl sulfate, and combinations thereof.

17. The method of claim 5, wherein the cationic surfactant is selected from the group consisting of benzalkonium chloride, benzethonium chloride, behentrimonium chloride, behentrimonium methosulfate, cetrimonium bromide, stearyl dimethylbenzyl ammonium chloride, a coconut amine, and combinations thereof.

18. The method of claim 1, wherein the one or more surfactants in the cosmetic formulation comprises a nonionic surfactant.

19. The method of claim 18, wherein the nonionic surfactant is selected from the group consisting of ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, poloxamers, stearoyl monoisopropanolamide, polyoxyethylene hydrogenated tallow amide, and combinations thereof.

20. The method of claim 1, wherein the one or more surfactants in the cosmetic formulation comprises a natural surface active agent.

21. The method of claim 20, wherein the natural surface active agent is selected from the group consisting of saponin, lecithin, soybean phospholipid, hydrogenated soybean phospholipid, soybean lysophospholipid, hydrogenated soybean lysophospholipid, egg yolk lecithin, hydrogenated egg yolk lysophosphatidylcholine, phosphatidylcholine, phosphatidylethanolamine, phosphatidylserine, sphingophospholipid, sphingomyelin, ganglioside, bile acid, cholic acid, deoxycholic acid, sodium cholate, sodium deoxycholate, spiculisporic acid, rhamnolipid, trehalose lipid, sophorolipid, mannosyl erythritol lipid, surfactin, salts thereof, and combinations thereof.

22. The method of claim 1, wherein the one or more surfactants in the cosmetic formulation comprises an amphoteric surfactant.

23. The method of claim 1, wherein the cosmetic formulation is provided in a kit comprising a first container and a second container, wherein the first container comprises the cosmetic formulation.

24. The method of claim 23, wherein the second container is a spray container.

25. The method of claim 23, wherein the second container comprises the cosmetically acceptable carrier.

26. The method of claim 23, further comprising adding the cosmetically acceptable carrier to the second container.

27. The method of claim 23, wherein the cosmetic formulation and the cosmetically acceptable carrier are mixed in the second container to form the hair treatment formulation.

28. The method of claim 27, wherein the hair treatment formulation is applied to damaged hair from the second container.

29. A method of treating hair to reduced or prevent breakage, comprising:
- mixing a cosmetic formulation with a cosmetically acceptable carrier to form a hair treatment formulation;
  - wherein the cosmetic formulation comprises bis(2-ethylhexyl) maleate, one or more surfactants and a cosmetically acceptable diluent, wherein the amount of bis(2-ethylhexyl) maleate in the cosmetic formulation is at least about 80% by weight, wherein the amount of the one or more surfactants in the cosmetic formulation is about 1-5% by weight, wherein the cosmetically acceptable diluent comprises an alcohol;
- wherein the water; and
- wherein the hair treatment formulation comprises at least about 50 wt. % of water; and
- applying the hair treatment formulation to damaged hair, wherein breakage of the hair is decreased by at least 5% compared to untreated hair.

30. The method of claim 29, wherein the amount of the alcohol in the cosmetic formulation is about 1-10% by weight.

* * * * *